United States Patent
Narasimha Rao et al.

(10) Patent No.: US 10,617,912 B2
(45) Date of Patent: Apr. 14, 2020

(54) SYSTEMS AND METHODS OF SWIMMING CALORIMETRY

(71) Applicant: Apple Inc., Cupertino, CA (US)

(72) Inventors: Bharath Narasimha Rao, Mountain View, CA (US); Craig H. Mermel, San Jose, CA (US); Karthik Jayaraman Raghuram, Mountain View, CA (US); Hung A. Pham, Oakland, CA (US); James P. Ochs, San Francisco, CA (US); Vinay R. Majjigi, Mountain View, CA (US); Alexander Singh Alvarado, Sunnyvale, CA (US); Sunny K. Chow, Santa Clara, CA (US); Umamahesh Srinivas, Milpitas, CA (US); Xing Tan, San Jose, CA (US); Robin T. Guers, Cupertino, CA (US); Adeeti Ullal, Mountain View, CA (US); Stephen P. Jackson, San Francisco, CA (US); Mrinal Agarwal, San Jose, CA (US)

(73) Assignee: Apple Inc., Cupertino, CA (US)

( * ) Notice: Subject to any disclaimer, the term of this patent is extended or adjusted under 35 U.S.C. 154(b) by 328 days.

(21) Appl. No.: 15/692,237

(22) Filed: Aug. 31, 2017

(65) Prior Publication Data

US 2018/0056129 A1  Mar. 1, 2018

Related U.S. Application Data

(60) Provisional application No. 62/382,060, filed on Aug. 31, 2016, provisional application No. 62/478,900, filed on Mar. 30, 2017.

(51) Int. Cl.
*A63B 24/00* (2006.01)
*A61B 5/11* (2006.01)
(Continued)

(52) U.S. Cl.
CPC ........ *A63B 24/0062* (2013.01); *A61B 5/0205* (2013.01); *A61B 5/02438* (2013.01);
(Continued)

(58) Field of Classification Search
CPC .......... A63B 24/00652; A63B 24/0006; A63B 2024/0071; A63B 2208/03;
(Continued)

(56) References Cited

U.S. PATENT DOCUMENTS

| 4,566,461 A | 1/1986 | Lubell et al. |
| 5,158,093 A | 10/1992 | Shvartz et al. |

(Continued)

FOREIGN PATENT DOCUMENTS

| GB | 2465824 | 6/2010 |
| IN | 259/KOL/2015 | 12/2015 |

(Continued)

OTHER PUBLICATIONS

Novatel, "IMU Error and Their Effects", Novatel Application Notes APN-064 Rev A p. 1-6, Feb. 21, 2014.
(Continued)

*Primary Examiner* — Manuel L Barbee
(74) *Attorney, Agent, or Firm* — DLA Piper LLP US

(57) ABSTRACT

The present disclosure relates to systems and methods of estimating energy expenditure of a user while swimming. A processor circuit of a user device can estimate a speed of the user based on a stroke rate and a stroke length. The processor circuit can estimate an efficiency of the user. The processor circuit can classify a swimming style of the user. The processor circuit can determine energy expenditure of the user based on the speed, the efficiency, and the style. The processor circuit can also detect glides of the user and adjust the energy expenditure.

19 Claims, 29 Drawing Sheets

(51) Int. Cl.
  *A61B 5/00* (2006.01)
  *A61B 5/0205* (2006.01)
  *A61B 5/024* (2006.01)

(52) U.S. Cl.
  CPC .......... *A61B 5/1112* (2013.01); *A61B 5/1114* (2013.01); *A61B 5/1121* (2013.01); *A61B 5/1123* (2013.01); *A61B 5/4866* (2013.01); *A61B 5/681* (2013.01); *A61B 5/7221* (2013.01); *A61B 5/7264* (2013.01); *A61B 5/7278* (2013.01); *A61B 5/7475* (2013.01); *A63B 24/0006* (2013.01); *A61B 2562/0219* (2013.01); *A63B 2024/0071* (2013.01); *A63B 2208/03* (2013.01); *A63B 2220/12* (2013.01); *A63B 2220/17* (2013.01); *A63B 2220/30* (2013.01); *A63B 2220/56* (2013.01); *A63B 2220/73* (2013.01); *A63B 2220/74* (2013.01); *A63B 2220/803* (2013.01); *A63B 2220/836* (2013.01); *A63B 2225/50* (2013.01); *A63B 2230/06* (2013.01); *A63B 2230/75* (2013.01)

(58) Field of Classification Search
  CPC ............ A63B 2220/12; A63B 2220/17; A63B 2220/30; A63B 2220/56; A63B 2220/73; A63B 2220/74; A63B 2220/803; A63B 2220/836; A63B 2225/50; A63B 2230/06; A63B 2230/75; A61B 5/0205; A61B 5/02438; A61B 5/1112; A61B 5/1114; A61B 5/1121; A61B 5/1123; A61B 5/4866; A61B 5/681; A61B 5/7221; A61B 5/7264; A61B 5/7478; A61B 5/7475; A61B 2562/0219
  See application file for complete search history.

(56) References Cited

U.S. PATENT DOCUMENTS

| | | | |
|---|---|---|---|
| 5,663,897 A * | 9/1997 | Geiser | A63B 71/0686 441/56 |
| 6,013,008 A | 1/2000 | Fukushima | |
| 6,059,724 A | 5/2000 | Campell et al. | |
| 6,582,380 B2 | 6/2003 | Kazlausky et al. | |
| 6,687,535 B2 | 2/2004 | Hautala et al. | |
| 6,837,827 B1 | 1/2005 | Lee et al. | |
| 7,254,516 B2 | 8/2007 | Case, Jr. et al. | |
| 7,311,675 B2 | 12/2007 | Peifer et al. | |
| 7,467,060 B2 | 12/2008 | Kulach et al. | |
| 7,534,206 B1 | 5/2009 | Lovitt et al. | |
| 7,690,556 B1 | 4/2010 | Kahn et al. | |
| 7,771,320 B2 | 8/2010 | Riley et al. | |
| 7,805,149 B2 | 9/2010 | Werner et al. | |
| 7,841,967 B1 | 11/2010 | Kahn et al. | |
| 8,290,480 B2 | 10/2012 | Abramson et al. | |
| 8,483,775 B2 | 7/2013 | Buck et al. | |
| 8,589,174 B2 | 11/2013 | Nelson et al. | |
| 8,892,391 B2 | 11/2014 | Tu et al. | |
| 8,894,576 B2 | 11/2014 | Alwan et al. | |
| 8,911,329 B2 | 12/2014 | Lin et al. | |
| 9,413,871 B2 | 8/2016 | Nixon et al. | |
| 9,526,430 B2 | 12/2016 | Srinivas et al. | |
| 9,788,794 B2 | 10/2017 | Le Boeuf et al. | |
| 10,188,347 B2 | 1/2019 | Self et al. | |
| 10,206,627 B2 | 2/2019 | Le Boeuf et al. | |
| 10,219,708 B2 | 3/2019 | Altini | |
| 10,292,606 B2 | 5/2019 | Wisbey et al. | |
| 2001/0022828 A1 | 9/2001 | Pyles | |
| 2002/0019585 A1 | 2/2002 | Dickinson | |
| 2003/0032460 A1 | 2/2003 | Cannon et al. | |
| 2004/0064061 A1 | 4/2004 | Nissila | |
| 2005/0107723 A1 | 5/2005 | Wehman et al. | |
| 2006/0064277 A1 | 3/2006 | Jung et al. | |
| 2006/0136173 A1 | 6/2006 | Case et al. | |
| 2006/0190217 A1 | 8/2006 | Lee et al. | |
| 2006/0217231 A1 | 9/2006 | Parks et al. | |
| 2007/0100666 A1 | 5/2007 | Stivoric et al. | |
| 2007/0150229 A1 | 6/2007 | Fujiwara | |
| 2007/0219059 A1 | 9/2007 | Schwartz et al. | |
| 2007/0275825 A1 | 11/2007 | O'Brien | |
| 2007/0276271 A1 | 11/2007 | Chan | |
| 2008/0096726 A1 | 4/2008 | Riley et al. | |
| 2008/0214360 A1 | 9/2008 | Stirling et al. | |
| 2009/0009320 A1 | 1/2009 | O'Connor et al. | |
| 2009/0024332 A1 | 1/2009 | Karlov et al. | |
| 2009/0043531 A1 | 2/2009 | Kahn et al. | |
| 2009/0063099 A1 | 3/2009 | Counts et al. | |
| 2010/0030350 A1 | 2/2010 | House et al. | |
| 2010/0130890 A1 | 5/2010 | Matsumura et al. | |
| 2010/0184564 A1 | 7/2010 | Molyneux et al. | |
| 2010/0204952 A1 | 8/2010 | Irlam et al. | |
| 2010/0210953 A1 | 8/2010 | Sholder et al. | |
| 2010/0210975 A1 | 8/2010 | Anthony, III et al. | |
| 2010/0217099 A1 | 8/2010 | Leboeuf et al. | |
| 2010/0274102 A1 | 10/2010 | Teixeira | |
| 2010/0298656 A1 | 11/2010 | McCombie et al. | |
| 2011/0040193 A1 | 2/2011 | Seppanen et al. | |
| 2011/0054359 A1 | 3/2011 | Sazonov et al. | |
| 2011/0082008 A1 | 4/2011 | Cheung et al. | |
| 2011/0131012 A1 | 6/2011 | Czaja et al. | |
| 2011/0152695 A1 | 6/2011 | Granqvist et al. | |
| 2011/0195707 A1 | 8/2011 | Faerber et al. | |
| 2011/0238485 A1 | 9/2011 | Haumont et al. | |
| 2011/0301436 A1 | 12/2011 | Teixeira | |
| 2012/0083715 A1 | 4/2012 | Friedman | |
| 2012/0172677 A1 | 7/2012 | Beith | |
| 2012/0238832 A1 | 9/2012 | Hwang | |
| 2012/0296455 A1 | 11/2012 | Ohnemus et al. | |
| 2012/0322621 A1 | 12/2012 | Bingham et al. | |
| 2013/0023739 A1 | 1/2013 | Russel | |
| 2013/0041590 A1 | 2/2013 | Burich et al. | |
| 2013/0053990 A1 | 2/2013 | Ackland | |
| 2013/0096943 A1 | 4/2013 | Carey et al. | |
| 2013/0158686 A1 | 6/2013 | Zhang et al. | |
| 2013/0178335 A1 | 7/2013 | Lin et al. | |
| 2013/0197377 A1 | 8/2013 | Takahiko et al. | |
| 2013/0218053 A1 | 8/2013 | Kaiser et al. | |
| 2013/0267794 A1 | 10/2013 | Fernstrom et al. | |
| 2014/0073486 A1 | 3/2014 | Ahmed et al. | |
| 2014/0087708 A1 | 3/2014 | Kalita et al. | |
| 2014/0088444 A1 | 3/2014 | Saalasti et al. | |
| 2014/0107932 A1 | 4/2014 | Luna | |
| 2014/0109390 A1 | 4/2014 | Manning | |
| 2014/0167973 A1 | 6/2014 | Letchner et al. | |
| 2014/0172238 A1 | 6/2014 | Craine | |
| 2014/0197946 A1 | 7/2014 | Park et al. | |
| 2014/0200906 A1 | 7/2014 | Bentley et al. | |
| 2014/0207264 A1 | 7/2014 | Quy | |
| 2014/0213920 A1 | 7/2014 | Lee et al. | |
| 2014/0221854 A1 | 8/2014 | Wai | |
| 2014/0228649 A1 | 8/2014 | Rayner et al. | |
| 2014/0244071 A1 | 8/2014 | Czaja et al. | |
| 2014/0266789 A1 | 9/2014 | Matus | |
| 2014/0276127 A1 | 9/2014 | Ferdosi et al. | |
| 2014/0278139 A1 | 9/2014 | Hong et al. | |
| 2014/0278229 A1 | 9/2014 | Hong et al. | |
| 2014/0316305 A1 | 10/2014 | Venkatraman et al. | |
| 2014/0348367 A1 * | 11/2014 | Vavrus | H04R 1/1091 381/334 |
| 2015/0087929 A1 | 3/2015 | Rapoport et al. | |
| 2015/0088006 A1 | 3/2015 | Rapoport et al. | |
| 2015/0100141 A1 | 4/2015 | Hughes | |
| 2015/0119728 A1 | 4/2015 | Blackadar et al. | |
| 2015/0148632 A1 | 5/2015 | Benaron | |
| 2015/0250417 A1 | 9/2015 | Cheng et al. | |
| 2015/0256689 A1 | 9/2015 | Erkkila et al. | |
| 2015/0260514 A1 | 9/2015 | Menelas et al. | |
| 2015/0327804 A1 | 11/2015 | Lefever et al. | |
| 2015/0328523 A1 | 11/2015 | Heling et al. | |
| 2015/0338926 A1 | 11/2015 | Park et al. | |
| 2015/0345985 A1 | 12/2015 | Fung et al. | |
| 2015/0355948 A1 | 12/2015 | Goldstein | |
| 2015/0374240 A1 | 12/2015 | Lee | |

(56) References Cited

U.S. PATENT DOCUMENTS

| | | |
|---|---|---|
| 2016/0021238 A1 | 1/2016 | Abramson et al. |
| 2016/0057372 A1 | 3/2016 | Raghuram et al. |
| 2016/0058302 A1 | 3/2016 | Raghuram et al. |
| 2016/0058329 A1 | 3/2016 | Srinivas et al. |
| 2016/0058332 A1 | 3/2016 | Tan et al. |
| 2016/0058333 A1 | 3/2016 | Arnold et al. |
| 2016/0058356 A1 | 3/2016 | Raghuram et al. |
| 2016/0058370 A1 | 3/2016 | Raghuram et al. |
| 2016/0058371 A1 | 3/2016 | Singh Alvarado et al. |
| 2016/0058372 A1 | 3/2016 | Raghuram et al. |
| 2016/0059079 A1 | 3/2016 | Watterson |
| 2016/0166178 A1 | 6/2016 | Fuss et al. |
| 2016/0170998 A1 | 6/2016 | Frank et al. |
| 2016/0206248 A1 | 7/2016 | Sartor |
| 2016/0256058 A1 | 9/2016 | Pham et al. |
| 2016/0269572 A1 | 9/2016 | Erkkila et al. |
| 2016/0287177 A1 | 10/2016 | Huppert et al. |
| 2016/0361020 A1 | 12/2016 | LeBoeuf et al. |
| 2016/0363449 A1 | 12/2016 | Metzler et al. |
| 2016/0374614 A1 | 12/2016 | Cavallaro et al. |
| 2017/0007166 A1 | 1/2017 | Roover et al. |
| 2017/0074897 A1 | 3/2017 | Mermel et al. |
| 2017/0082649 A1 | 3/2017 | Tu et al. |
| 2017/0094450 A1 | 3/2017 | Tu et al. |
| 2017/0111768 A1 | 4/2017 | Smith et al. |
| 2017/0188893 A1 | 7/2017 | Venkatraman et al. |
| 2017/0202486 A1 | 7/2017 | Martikka et al. |
| 2017/0251972 A1 | 9/2017 | Jayaraman et al. |
| 2017/0259116 A1 | 9/2017 | Mestas |
| 2017/0273619 A1 | 9/2017 | Alvarado et al. |
| 2017/0347885 A1 | 12/2017 | Tan et al. |
| 2017/0367658 A1 | 12/2017 | LeBoeuf et al. |
| 2018/0049694 A1 | 2/2018 | Singh Alvarado et al. |
| 2018/0050235 A1 | 2/2018 | Tan et al. |
| 2018/0055375 A1 | 3/2018 | Martinez et al. |
| 2018/0055439 A1 | 3/2018 | Pham et al. |
| 2018/0056123 A1 | 3/2018 | Narasimha Rao et al. |
| 2018/0056128 A1 | 3/2018 | Narasimha Rao et al. |

FOREIGN PATENT DOCUMENTS

| | | |
|---|---|---|
| JP | 2010-051333 A | 3/2010 |
| JP | 2013-039316 A | 2/2013 |
| JP | 2014-042757 A | 3/2014 |
| JP | 2016-150018 A | 8/2016 |
| JP | 2018-000543 A | 1/2018 |
| JP | 2018-015187 A | 2/2018 |
| WO | 2010090867 | 8/2010 |
| WO | 2011/105914 A1 | 9/2011 |
| WO | 2015/126182 A1 | 8/2015 |
| WO | 2015/200900 A1 | 12/2015 |
| WO | 2016/044831 A1 | 3/2016 |
| WO | 2016/073620 A1 | 5/2016 |

OTHER PUBLICATIONS

KINprof, May 31, 2011, Predictive VO2max tests, Web Video, Retrieved from: https://www.youtube.com/watch?v=_9e3HcY1sm8.
PCT International Application No. PCT/US2017/049693, International Search Report dated Aug. 12, 2017, 3 pages.
Le, et al., "Sensor-based Training Optimization of a Cyclist Group", Seventh International Conference on Hybrid Intelligent Systems, IEEE 2007, pp. 265-270.
Yamaji, et al., "Relationship Between Heart Rate and Relative Oxygen Intake in Male Subjects Aged 10 to 27 Years", J. Human Ergol., 7:29-39, Jan. 27, 1978.
Your Fitness FAQ, Why is it important to warm up and cool down in a workout?, 2012, Web, Retrieved from: http://www.yourfitnessfaq.com/whyisitimportanttowarmupandcooldowninaworkout.html.
Vella et al, Exercise After-Burn: Research Update, 2005, Web, Retrieved from: http://www.unm.edu/~lkravitz/Article%20folder/epocarticle.html.
Song et al., "Training Activity Recognition Systems Online Using Real-Time Crowdsourcing", University of Rochester Computer Science, UbiCom' 12, Sep. 5-8, 2012 (2 pages).
Rowlands et al., "Assessing Sedentary Behavior with the GENEActiv: Introducing the Sedentary Sphere". Medicine and science in sports and exercise 46.6 (2014): 1235-1247.
Hasson et al., "Accuracy of four resting metabolic rate production equations: Effects of sex, body mass index, age, and race/ethnicity", Journal of Science and Medicine in Sport, 2011, vol. 14, p. 344-351.
Lucas et al., "Mechanisms of orthostatic intolerance following very prolonged exercise", 2008, J Appl Physiol, 105: 213-225.
Kunze et al., "Where am i: Recognizing on-body positions of wearable sensors." Location-and context-awareness. Springer Berlin Heidelberg, 2005. 264-275.
Keytel et al., "Prediction of energy expenditure from heart rate monitoring during submaximal exercise", 2005, Journal of Sports Sciences, 23(3):289-97.
Sabatini, Kalman-filter orientation determination using inertial/magnetic sensors: observability analysis and performance evaluation, Sep. 27, 2011, Sensors 2011, 11, 9182-9206.
Jackson et al., "Prediction of functional aerobic capacity without exercise testing", Medicine and Science in Sports and Exercise, 22(6), 863-870, 1990.
Isaacs et al., "Modeling energy expenditure and oxygen consumption in human exposure models: accounting for fatigue and EPOC", 2008, Journal of Exposure Science and Environmental Epidemiology, 18: 289-298.
Human Kinetics, Aerobic Workout Components, 2011, Web, Retrieved from: http://www.humankinetics.com/excerpts/excerpts/aerobicworkoutcomponentsexcerpt.
Gao et al., "Evaluation of accelerometer based multi-sensor versus single-sensor activity recognition systems." Medical engineering & physics 36.6 (2014): 779-785.
Frankenfield et al., "Comparison of Predictive Equations for Resting Metabolic Rate in Healthy Nonobese and Obese adults: A systematic review". Journal of the American Dietetic Association. May 2005, vol. 105, No. 5, p. 775-789.
Chu, "In-Vehicle Driver Detection Using Mobile Phone Sensors", Submitted for Graduation with departmental Distinction in Electrical and Computer Engineering, Apr. 20, 2011, pp. 1-21.
Bo et al., "TEXIVE: Detecting Drivers Using Personal Smart Phones by Leveraging Inertial Sensors", Department of Computer Science, Illinois Institute of Technology, Chicago IL, Dec. 7, 2014, pp. 1-12.
Brooks, G.A. et al., "Exercise Physiology: Human Bioenergetics and Its Applications," Fourth Edition, McGraw Hill, ISBN 0-07-255642-0, Chapter 2: Bioenergetics, Chapter 10: Metabolic Response to Exercise: Lactate Metabolism During Exercise and Recovery, Excess Postexercise O2 Consumption (EPOC), O2 Deficit, O2 Debt, and the Anaerobic Threshold, Chapter 16: Cardiovascular Dynamics During Exercise, Chapter 21: Principles of Endurance Conditioning, Chapter 27: Exercise Testing and Prescription, 141 pages (2004).
Bruce, R.A. et al., "Exercising testing in adult normal subjects and cardiac patients," Pediatrics, vol. 32, No. Suppl., pp. 742-756 (Oct. 1963).
Bruce, R.A. et al., "Maximal oxygen intake and nomographic assessment of functional aerobic impairment in cardiovascular disease," American Heart Journal, vol. 85, Issue 4, pp. 546-562 (Apr. 1973).
Burke, Edmund R., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 10: Physiology of Professional Road Cycling, Chapter 11: Physiology of Mountain Biking, 131 pages (2003).
Cavanagh, P.R. et al., "The effect of stride length variation on oxygen uptake during distance running," Medicine and Science in Sports and Exercise, vol. 14, No. 1, pp. 30-35 (1982).
Earnest, C.P. et al., "Cross-sectional association between maximal estimated cardiorespiratory fitness, cardiometabolic risk factors and metabolic syndrome for men and women in the Aerobics Center Longitudinal Study," Mayo Clin Proceedings, vol. 88, No. 3, pp. 259-270, 20 pages (Mar. 2013).

(56) References Cited

OTHER PUBLICATIONS

Fox, S.M. et al., "Physical Activity and the Prevention of Coronary Heart Disease," Bull. N.Y. Acad. Med., vol. 44, No. 8, pp. 950-967 (Aug. 1968).

Glass, S., et al., "ACSM's Metabolic Calculations Handbook," Lippincott Williams & Wilkins, 124 pages (2007).

Lavie, C.J. et al., "Impact of cardiorespiratory fitness on the obesity paradox in patients with heart failure," Mayo Clinic Proceedings, vol. 88, No. 3, pp. 251-258 (Mar. 2013).

Margaria, R. et al., "Energy cost of running," Journal of Applied Physiology, vol. 18, No. 2, pp. 367-370 (Mar. 1, 1963).

McArdle, W.D. et al., "Exercise Physiology: Nutrition, Energy and Human Performance," Seventh Edition, Lippincott Williams & Wilkins, Chapter 5: Introduction to Energy Transfer, Chapter 6: Energy Transfer in the Body, Chapter 7: Energy Transfer During Exercise, Chapter 8: Measurement of Human Energy Expenditure, Chapter 9: Human Energy Expenditure During Rest and Physical Activity, Chapter 10: Energy Expenditure During Walking, Jogging, Running and Swimming, Chapter 11: Individual Differences and Measurement of Energy Capacities, Chapter 21: Training for Anaerobic and Aerobic Power, 184 page (2010).

Myers, J. et al., "Exercise Capacity and Mortality Among Men Referred for Exercise Testing," The New England Journal of Medicine, vol. 346, No. 11, pp. 793-801 (Mar. 14, 2002).

Noakes, Timothy D., "Lore of Running," Fourth Edition, Human Kinetics, Chapter 2: Oxygen Transport and Running Economy, Chapter 3: Energy Systems and Running Performance, 157 pages (2002).

Rapoport, Benjamin I., "Metabolic Factors Limiting Performance in Marathon Runners," PLoS Computational Biology, vol. 6, Issue 10, 13 pages (Oct. 2010).

Tanaka, H. et al., "Age-predicted maximal heart rate revisited," Journal of the American College of Cardiology, vol. 37, Issue 1, pp. 153-156 (Jan. 2001).

Wang, L. et al., "Time constant of heart rate recovery after low level exercise as a useful measure of cardiovascular fitness," Conf. Proc. IEEE Eng. Med. Biol. Soc., vol. 1, pp. 1799-1802 (2006).

International Search Report and Written Opinion received for PCT Patent Application No. PCT/US2018/047290, dated Nov. 8, 2018, 14 pages.

Kyle, Chester R., "Reduction of Wind Resistance and Power Output of Racing Cyclists and Runners Travelling in Groups", Ergonomics, vol. 22, No. 4, 1979, pp. 387-397.

* cited by examiner

SYSTEMS AND METHODS OF SWIMMING CALORIMETRY

PRIORITY CLAIM

This application claims priority to and the benefit of U.S. Provisional Patent Application No. 62/382,060, titled "System and Methods for Swimming Calorimetry," which was filed on Aug. 31, 2016 and is incorporated by reference herein in its entirety.

This application claims priority to and the benefit of U.S. Provisional Patent Application No. 62/478,900, titled "Swimming Glide Detection," which was filed on Mar. 30, 2017 and is incorporated by reference herein in its entirety.

CROSS-REFERENCE TO RELATED APPLICATIONS

This application relates to co-pending U.S. patent application Ser. No. 15/691,245, titled "Systems and Methods for Determining Swimming Metrics," which is filed on Aug. 30, 2017 and is incorporated by reference herein in its entirety.

This application related to co-pending U.S. patent application Ser. No. 15/692,726, titled "Systems and Methods of Swimming Analysis," which is filed on Aug. 31, 2017 and is incorporated by reference herein in its entirety.

FIELD

The present disclosure relates generally to swimming calorimetry.

BACKGROUND

When a user is swimming, there is often a need to know many factors related to the swimming session, such as total distances, number of laps, swimming styles, stroke consistency, and/or energy expenditure. It is, however, generally difficult to estimate how many calories a user burns during a swimming session because energy expenditure depends on many factors such as speed, efficiency, swimming style, etc. Particularly, glides and strokes can correspond to different energy consumption rates, and ignoring glides can cause overestimates in energy expenditure. Accordingly, it is desirable to provide methods and systems for estimating energy expenditure of a user while swimming.

SUMMARY

The present disclosure relates to a method for improving an accuracy of a wearable device while estimating energy expenditure of a user during a swimming session. In some embodiments, the method can include: collecting, by a motion sensing module of a wearable device, motion data of the user; determining, by a processor circuit of the wearable device, rotational data of the user based on the motion data; counting, by the processor circuit, a number of strokes made by the user based on the set of rotational data; estimating, by the processor circuit, a stroke rate of the user based on the number of strokes; counting, by the processor circuit, a number of laps finished by the user based on the set of rotational data; calculating, by the processor circuit, a stroke length based on the number of strokes, the number of laps finished, and a lap length associated with the swimming session; calculating, by the processor circuit, a speed of the user based on the stroke rate and the stroke length; estimating, by the processor circuit, an efficiency of the user based on at least one of the stroke length or a level of stroke orbit consistency of the user; classifying, by the processor circuit, a swimming style of the user based on the set of rotational data; determining, by the processor circuit, an energy expenditure of the user based on the speed, efficiency, and swimming style of the user; and outputting, by the processor circuit, the determined energy expenditure of the user. In some embodiments, the motion data can be expressed in a first frame of reference and the rotation data can be expressed in a second frame of reference.

In some embodiments, the method can include receiving one or more inputs form the user; adjusting the energy expenditure of the user based on the received one or more inputs; and outputting the adjusted energy expenditure of the user. In some embodiments, the one or more inputs from the user can include at least one of the user's gender, age, height, weight, or body mass index.

In some embodiments, the method can include measuring, by a heart rate sensing module of the wearable device, a heart rate of the user; determining a fraction of heart rate reserve (FHR) of the user based on the measured heart rate; estimating, by the processor circuit, the user's anaerobic energy expenditure based on at least one of the user's fraction of heart rate reserve, stroke length, stroke rate, and or speed; and determining, by the processor circuit, the energy expenditure of the user based on the estimated anaerobic energy expenditure.

In some embodiments, the method can include: measuring, by a heart rate sensing module of the wearable device, a heart rate of the user; determining, by the processor circuit, a fraction of heart rate reserve (FHR) of the user based on the measured heart rate; determining, by the processor circuit, a maximal oxygen uptake of the user; determining, by the processor circuit, a heart rate model based on FHR and the maximal oxygen uptake, wherein determining the energy expenditure of the user based on the heart rate model.

In some embodiments, the method can include: receiving, by a GPS sensor of the wearable device, location data of the user during the swimming session; and calculating, by the processor circuit, a stroke length and a speed of the user based on the received location data. In some embodiments, the motion sensing module can include at least one of a gyroscope or an accelerometer.

In some embodiments, the method can include: detecting, by the processor circuit, one or more glides of the user during the swimming session; and determining, by the processor circuit, the energy expenditure of the user based on the detected one or more glides. In some embodiments, the method can include: determining, by the processor circuit, whether the user is making a turn based on the set of rotational data; detecting, by the processor circuit, a pose angle of the user's wrist based on the set of rotational data; determining, by the processor circuit, whether the user is under water using pressure data received from a pressure sensor of the wearable device; detecting, by the processor circuit, one or more glides of the user based on the stroke rate, the pose angle of the user's wrist, whether the user is making a turn, and whether the user is under water.

In some embodiments, the method can include: determining, by the processor circuit, a direction of gravity relative to the user device based on the motion data; detecting, by the processor circuit, a pose of the user's wrist based on the direction of gravity.

In some embodiments, the method can include: receiving, by the processor circuit, pressure data from a pressure sensor of the wearable device; determining, by the processor circuit, an elevation of the wearable device based on the pressure data; and determining, by the processor circuit, whether the user is under water based on the determined elevation.

The present disclosure also relates to a system for improving an accuracy of a wearable device while estimating energy expenditure of a user during a swimming session. In some embodiments, the system can include: a motion sensing module configured to collect motion data of the user; a processor circuit in communication with the motion sensing module and configured to execute instructions causing the processor circuit to: determine rotational data of the user base on the motion data; count a number of strokes made by the user based on the set of rotational data; estimate a stroke rate of the user based on the number of strokes; count a number of laps finished by the user based on the set of rotational data; estimate a stroke length based on the number of strokes, the number of laps, and a length associated with the swimming session; estimate a speed of the user based on the stroke rate and the stroke length; estimate efficiency of the user based on at least one of the stroke length or a level of stroke orbit consistency of the user; classify a swimming style of the user based on the set of rotational data; determine an energy expenditure of the user based on the speed, efficiency, and swimming style of the user; and output the determined energy expenditure of the user.

In some embodiments, the system can include a heart rate sensing module configured to measure a heart rate of the user. In some embodiments, the instructions can further cause the processor circuit to: determine, a fraction of heart rate reserve (FHR) of the user based on the measured heart rate; determine, a maximal oxygen uptake of the user; determine, a heart rate model based on the FHR and the maximal oxygen uptake; and determine the energy expenditure of the user based on the heart rate model.

Other features and advantages will become apparent from the following detailed description and drawings.

BRIEF DESCRIPTION OF THE DRAWINGS

Various objects, features, and advantages of the present disclosure can be more fully appreciated with reference to the following detailed description of the present disclosure when considered in connection with the following drawings, in which like reference numerals identify like elements.

DETAILED DESCRIPTION

In the following description, numerous specific details are set forth regarding the systems, methods and media of the present disclosure and the environment in which such systems, methods and media may operate, etc., in order to provide a thorough understanding of the present disclosure. It will be apparent to one skilled in the art, however, that the present disclosure may be practiced without such specific details, and that certain features, which are well known in the art, are not described in detail in order to avoid complication of the present disclosure. In addition, it will be understood that the examples provided below are exemplary, and that it is contemplated that there are other systems, methods, and media that are within the scope of the present disclosure.

The present disclosure describes a wearable device (or a "user device") that may be configured to determine consistency of a user's stroke orbits while the user is swimming. The wearable device can include one or more motion sensors to collect data about the wearable device's position and orientation in space and to track changes to the wearable device's position and orientation over time. Because a user can wear the wearable device, the motion information can provide information about the user's movements. For example, when a user is swimming, the user's arms are typically swinging along a particular path and at a particular frequency. If the user wears the wearable device on the user's wrist, the wearable device may be able to infer that the user is swimming in a certain style and/or changing in direction by sensing the way the user's arm moves in a certain path. When the user is swimming, there is a fairly periodic motion of the user's arm/wrist that can be tracked by the wearable device. For example, the user may take a breath every stroke, or every suitable number of strokes (e.g., every two strokes, every three strokes, every four strokes, etc.)

Figure 1:
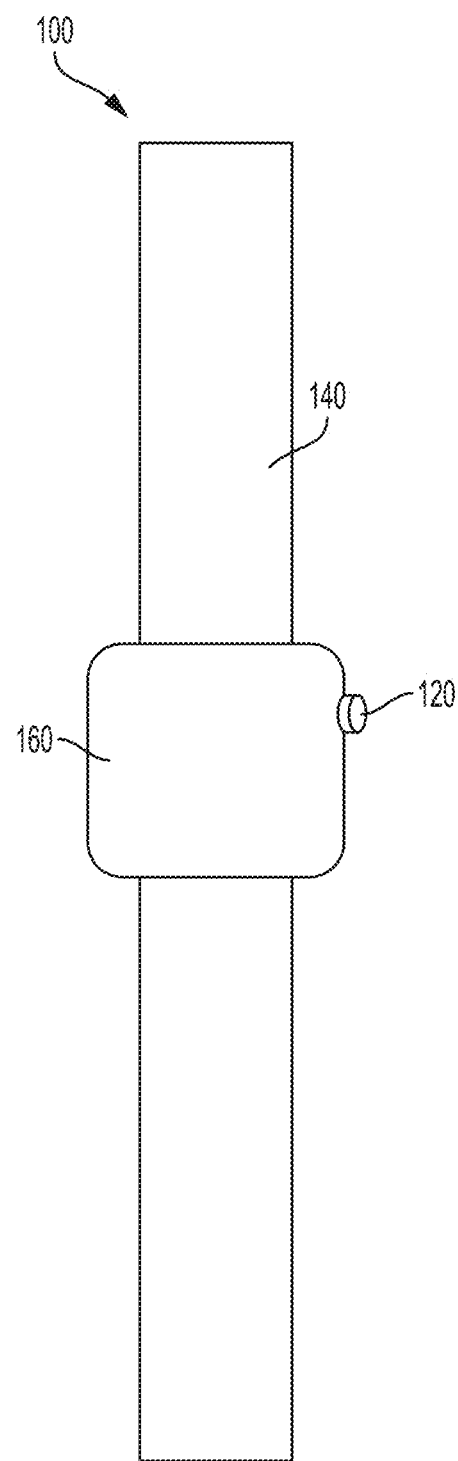
FIG. 1 illustrates a wearable device according to some embodiments of the present disclosure.

FIG. 1 shows an example of a wearable device (or a "user device") 100 according to some embodiments of the present disclosure. In some embodiments, wearable device 100 may be any suitable wearable device, such as a watch and/or a fitness band configured to be worn around an individual's wrist. In some embodiments, wearable device 100 includes a crown 120, a band 140, and/or a display surface 160.

Figure 2:
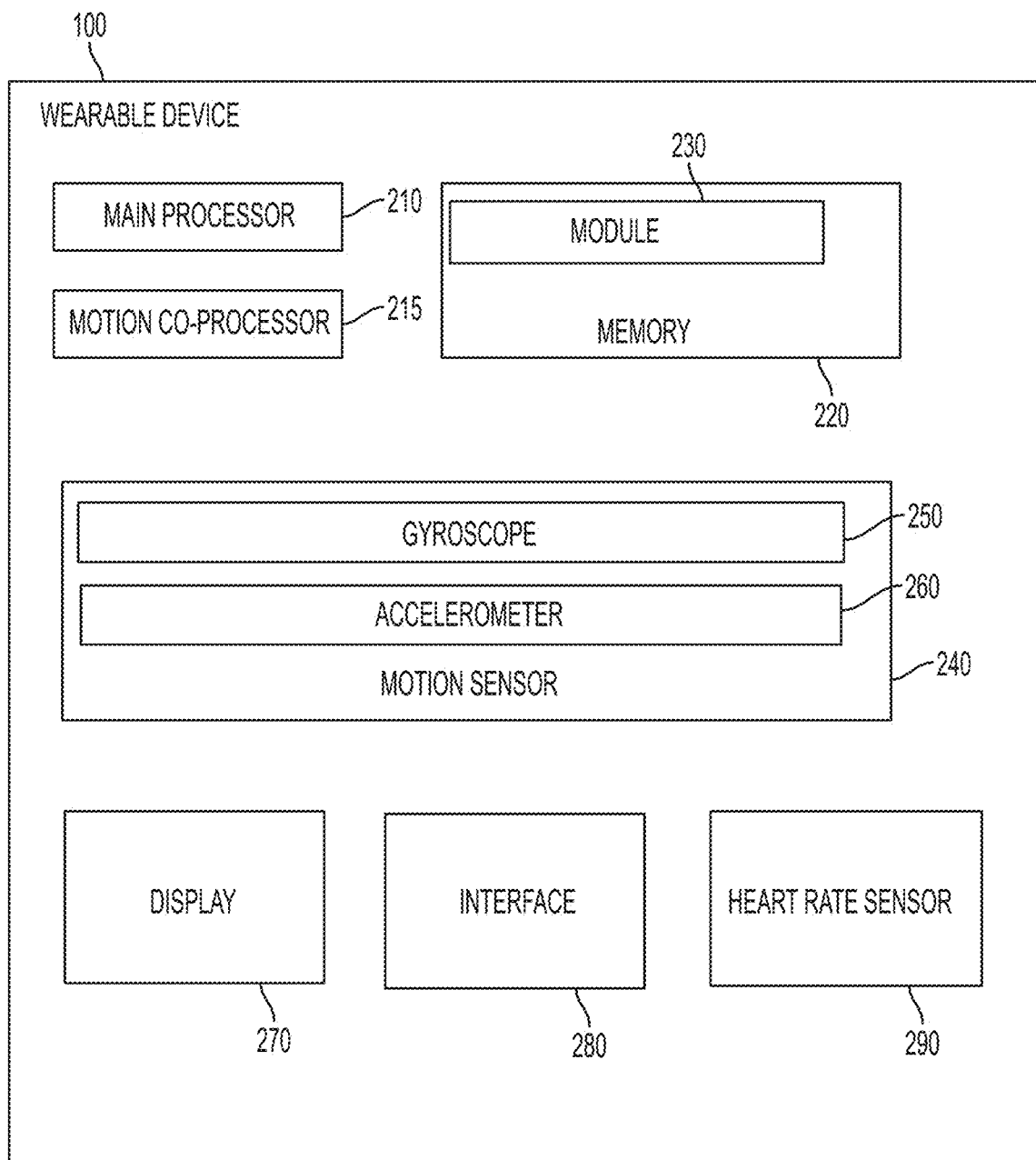
FIG. 2 illustrates a block diagram of a wearable device according to some embodiments of the present disclosure.

FIG. 2 depicts a block diagram of exemplary components that may be found within wearable device 100 according to some embodiments of the present disclosure. In some embodiments, wearable device 100 can include a main processor 210 (or "application processor"), a motion co-processor 215, a memory 220, one or more motion sensors 240, a display 270, an interface 280, and a heart rate sensor 290. Wearable device 100 may include additional modules, fewer modules, or any other suitable combination of modules that perform any suitable operation or combination of operations.

In some embodiments, main processor 210 can include one or more cores and can accommodate one or more threads to run various applications and modules. Software can run on main processor 210 capable of executing computer instructions or computer code. Main processor 210 can also be implemented in hardware using an application specific integrated circuit (ASIC), programmable logic array (PLA), field programmable gate array (FPGA), or any other integrated circuit.

In some embodiments, wearable device 100 also includes motion co-processor 215 which may draw less power than the main processor 210. Whereas the main processor 210 may be configured for general purpose computations and communications, the motion co-processor 215 may be configured to perform a relatively limited set of tasks, such as receiving and processing data from motion sensor 240, heart rate sensor 290, and other modules within the wearable device 100. In many embodiments, the main processor 210 may be powered down at certain times to conserve power, while the motion co-processor 215 remains powered on. Thus, the motion co-processor 215 is sometimes referred to as an "always-on" processor (AOP). Motion co-processor 215 may control when the main processor 210 is powered on or off.

Memory 220 can be a non-transitory computer readable medium, flash memory, a magnetic disk drive, an optical drive, a programmable read-only memory (PROM), a read-only memory (ROM), or any other memory or combination of memories. Memory 220 can include one or more modules 230.

Main processor 210 or motion co-processor 215 can be configured to run module 230 stored in memory 220 that is configured to cause main processor 210 or motion co-processor 215 to perform various steps that are discussed throughout the present disclosure.

In some embodiments, wearable device 100 can include one or more motion sensors 240. For example, motion sensors 240 can include a gyroscope 250 and an accelerometer 260. In some embodiments, accelerometer 260 may be a three-axis accelerometer that measures linear acceleration in up to three-dimensions (for example, x-axis, y-axis, and z-axis). In some embodiments, gyroscope 250 may be a three-axis gyroscope that measures rotational data, such as rotational movement and/or angular velocity, in up to three-dimension (for example, yaw, pitch, and roll). In some embodiments, accelerometer 260 may be a microelectromechanical system (MEMS) accelerometer, and gyroscope 250 may be an MEMS gyroscope. Main processor 210 or motion co-processor 215 of wearable device 100 may receive motion information from one or more motion sensors 240 to track acceleration, rotation, position, or orientation information of wearable device 100 in six degrees of freedom through three-dimensional space.

In some embodiments, wearable device 100 may include other types of sensors in addition to accelerometer 260 and gyroscope 250. For example, wearable device 100 may include an altimeter or barometer, or other types of location sensors, such as a GPS sensor.

Wearable device 100 may also include display 270. Display 270 may be a screen, such as a crystalline (e.g., sapphire) or glass touchscreen, configured to provide output to the user as well as receive input from the user via touch. For example, display 270 may be configured to display a current heart rate or daily average energy expenditure. Display 270 may receive input from the user to select, for example, which information should be displayed, or whether the user is beginning a physical activity (e.g., starting a session) or ending a physical activity (e.g., ending a session), such as a swimming session, a running session, or a cycling session. In some embodiments, wearable device 100 may present output to the user in other ways, such as by producing sound with a speaker (not shown), and wearable device 100 may receive input from the user in other ways, such as by receiving voice commands via a microphone (not shown).

In some embodiments, wearable device 100 may communicate with external devices via interface 280, including a configuration to present output to a user or receive input from a user. Interface 280 may be a wireless interface. The wireless interface may be a standard Bluetooth (IEEE 802.15) interface, such as Bluetooth v4.0, also known as "Bluetooth low energy." In other embodiments, the interface may operate according to a cellphone network protocol such as Long Term Evolution (LTE) or a Wi-Fi (IEEE 802.11) protocol. In other embodiments, interface 280 may include wired interfaces, such as a headphone jack or bus connector (e.g., Lightning, Thunderbolt, USB, etc.).

Wearable device 100 can measure an individual's current heart rate from heart rate sensor 290. Heart rate sensor 290 may also be configured to determine a confidence level indicating a relative likelihood of an accuracy of a given heart rate measurement. In other embodiments, a traditional heart rate monitor may be used and may communicate with wearable device 100 through a near field communication method (e.g., Bluetooth).

Wearable device 100 may be configured to communicate with a companion device 300 (FIG. 3), such as a smartphone, as described in more detail herein. In some embodiments, wearable device 100 may be configured to communicate with other external devices, such as a notebook or desktop computer, tablet, headphones, Bluetooth headset, etc.

The modules described above are examples, and embodiments of wearable device 100 may include other modules not shown. For example, some embodiments of wearable device 100 may include a rechargeable battery (e.g., a lithium-ion battery), a microphone or a microphone array, one or more cameras, one or more speakers, a watchband, water-resistant casing or coating, etc. In some embodiments, all modules within wearable device 100 can be electrically and/or mechanically coupled together. In some embodiments, main processor 210 can coordinate the communication among each module.

Figure 3:
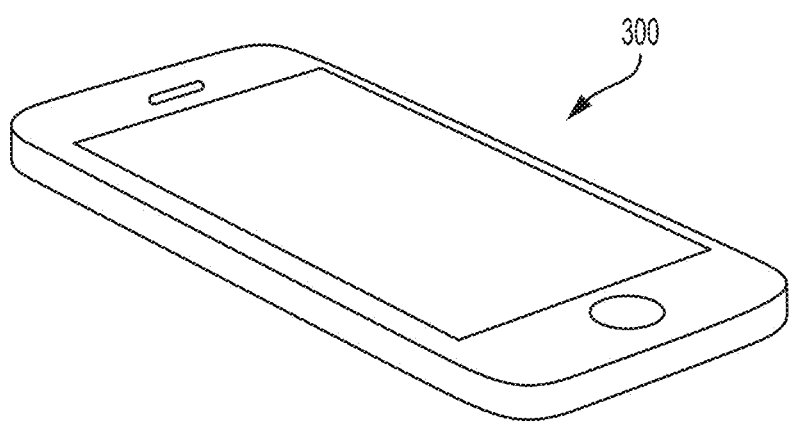
FIG. 3 illustrates a companion device according to some embodiments of the present disclosure.

FIG. 3 shows an example of a companion device 300 according to some embodiments of the present disclosure. Wearable device 100 may be configured to communicate with companion device 300 via a wired or wireless communication channel (e.g., Bluetooth, Wi-Fi, etc.). In some embodiments, companion device 300 may be a smartphone, tablet computer, or similar portable computing device. Companion device 300 may be carried by the user, stored in the user's pocket, strapped to the user's arm with an armband or similar device, placed in a mounting device, or otherwise positioned within communicable range of wearable device 100.

In some embodiments, companion device 300 may include a variety of sensors, such as location and motion sensors (not shown). When companion device 300 is available for communication with wearable device 100, wearable device 100 may receive additional data from companion device 300 to improve or supplement its calibration or calorimetry processes. For example, in some embodiments, wearable device 100 may not include a GPS sensor as opposed to an alternative embodiment in which wearable device 100 may include a GPS sensor. In the case where wearable device 100 may not include a GPS sensor, a GPS sensor of companion device 300 may collect GPS location information, and wearable device 100 may receive the GPS location information via interface 280 (FIG. 2) from companion device 300.

In another example, wearable device 100 may not include an altimeter or barometer, as opposed to an alternative embodiment in which wearable device 100 may include an altimeter or barometer. In the case where wearable device 100 may not include an altimeter or barometer, an altimeter or barometer of companion device 300 may collect altitude or relative altitude information, and wearable device 100 may receive the altitude or relative altitude information via interface 280 (FIG. 2) from the companion device 300.

In another example, wearable device 100 may receive motion information from companion device 300. Wearable device 100 may compare the motion information from companion device 300 with motion information from one or more motion sensors 240 of wearable device 100. Motion information such as data from accelerometer 260 and/or gyroscope 250 may be filtered (e.g. by a high-pass, low-pass, band-pass, or band-stop filter) in order to improve the quality of motion information. For example, a low-pass filter may be used to remove some ambient noise.

Wearable device 100 may use sensed and collected motion information to predict a user's activity. Examples of activities may include, but are not limited to, walking, running, cycling, swimming, etc. Wearable device 100 may also be able to predict or otherwise detect when a user is sedentary (e.g., sleeping, sitting, standing still, driving or otherwise controlling a vehicle, etc.) Wearable device 100 may use a variety of motion information, including, in some embodiments, motion information from a companion device.

Wearable device 100 may use a variety of heuristics, algorithms, or other techniques to predict the user's activity. Wearable device 100 may also estimate a confidence level (e.g., percentage likelihood, degree of accuracy, etc.) associated with a particular prediction (e.g., 90% likelihood that the user is running) or predictions (e.g., 60% likelihood that the user is running and 40% likelihood that the user is walking).

Figure 4:
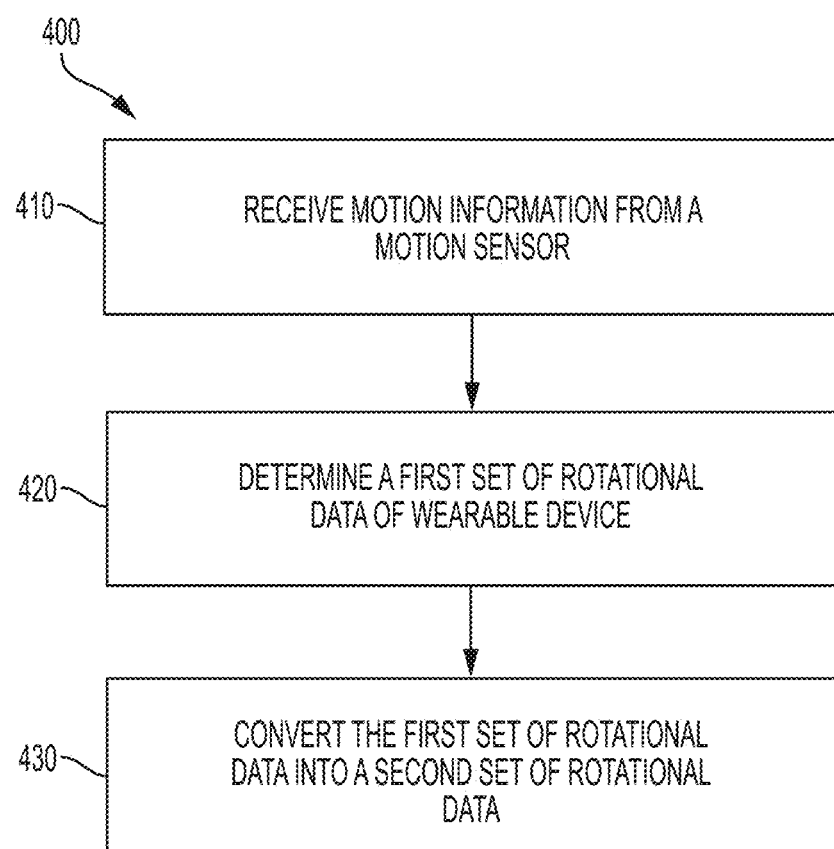
FIG. 4 illustrates a method of determining rotational data of a user while swimming according to some embodiments of the present disclosure.

FIG. 4 shows a flow chart illustrating a process 400 of determining one or more breaths taken by a user while swimming according to some embodiments of the present disclosure. In some embodiments, the process 400 can be modified by, for example, having steps combined, divided, rearranged, changed, added, and/or removed. As described in more details below, in some embodiments, the process 400 can include three steps. At step 410, wearable device 100 receives motion information from one or more motion sensors 240. At step 420, wearable device 100 determines a first set of rotational data of wearable device 100. At step 430, wearable device 100 converts the first set of rotational data into a second set of rotational data, where the second set of rotational data include pitch rotational data.

At step 410, motion information may be received from one or more motion sensors 240 on wearable device 100. In some embodiments, motion information may include three-dimensional rotational data of wearable device 100 from gyroscope 250. In some embodiments, motion information may include three-dimensional accelerations of wearable device 100 from accelerometer 260.

At step 420, wearable device 100 may determine a first set of rotational data of wearable device 100 based on the motion information received from one or more motion sensors 240. In some embodiments, the rotational data of wearable device 100 include how wearable device 100 rotates, such as angular position, angular velocity, and/or angular acceleration of wearable device 100, with respect to a frame of reference. In some embodiments, if the rotational data of wearable device 100 is angular acceleration, then angular velocity and/or angular position can be obtained by integrating the angular acceleration over time. Likewise, if the rotational data of wearable device 100 is angular velocity, then angular position can be obtained by integrating the angular velocity over time. In some embodiments, the first set of rotational data is received from gyroscope 250 and is expressed in a body-fixed frame of reference with respect to wearable device 100.

Figure 5A:
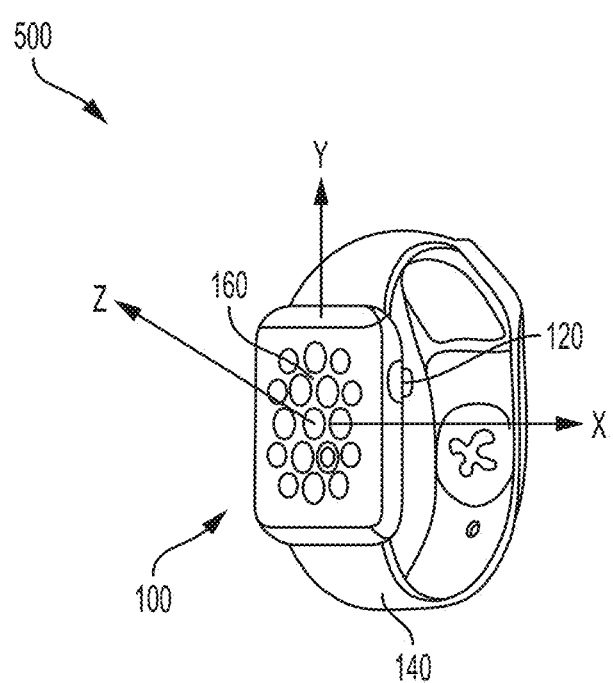
FIGS. 5A-5D illustrate an example of a body-fixed frame of reference according to some embodiments of the present disclosure.

FIG. 5A illustrates an example of a body-fixed frame of reference 500 according to some embodiments of the present disclosure. In FIG. 5A, the rotational axes of body-fixed frame of reference 500 are with respect to wearable device 100. For example, the z-axis is perpendicular to the display surface 160 of wearable device 100. The x-axis and the y-axis can be chosen relatively arbitrarily as long as the three axes are perpendicular to each other. In FIG. 5A, the x-axis is parallel with the direction pointed by crown 120 of wearable device 100, and the y-axis is parallel with the direction of band 140 of wearable device 100 (assuming the direction pointed by crown 120 of wearable device 100 is perpendicular to the direction of band 140 of wearable device 100).

Figure 5B:
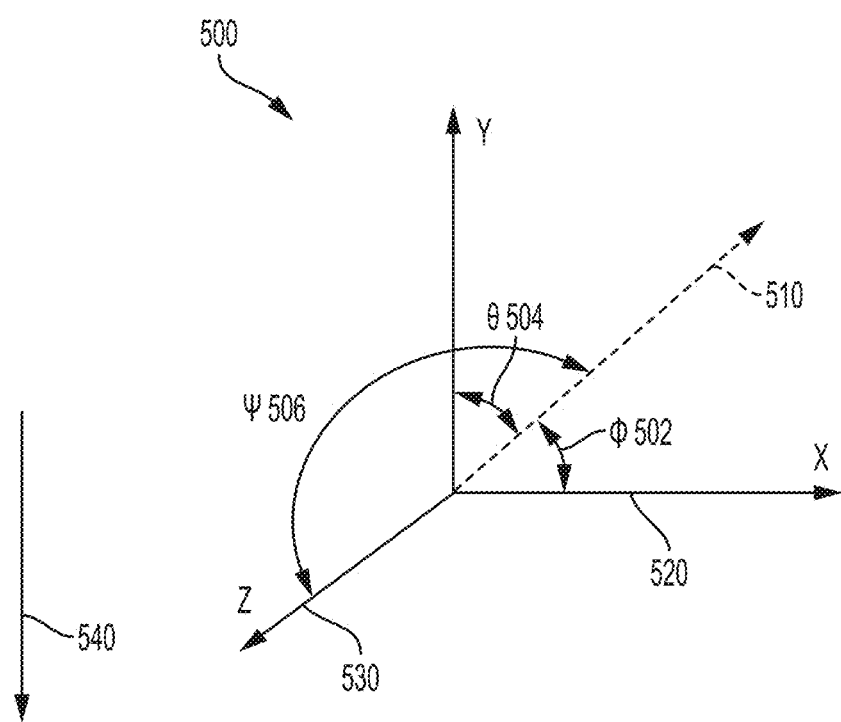
Figure 5C:
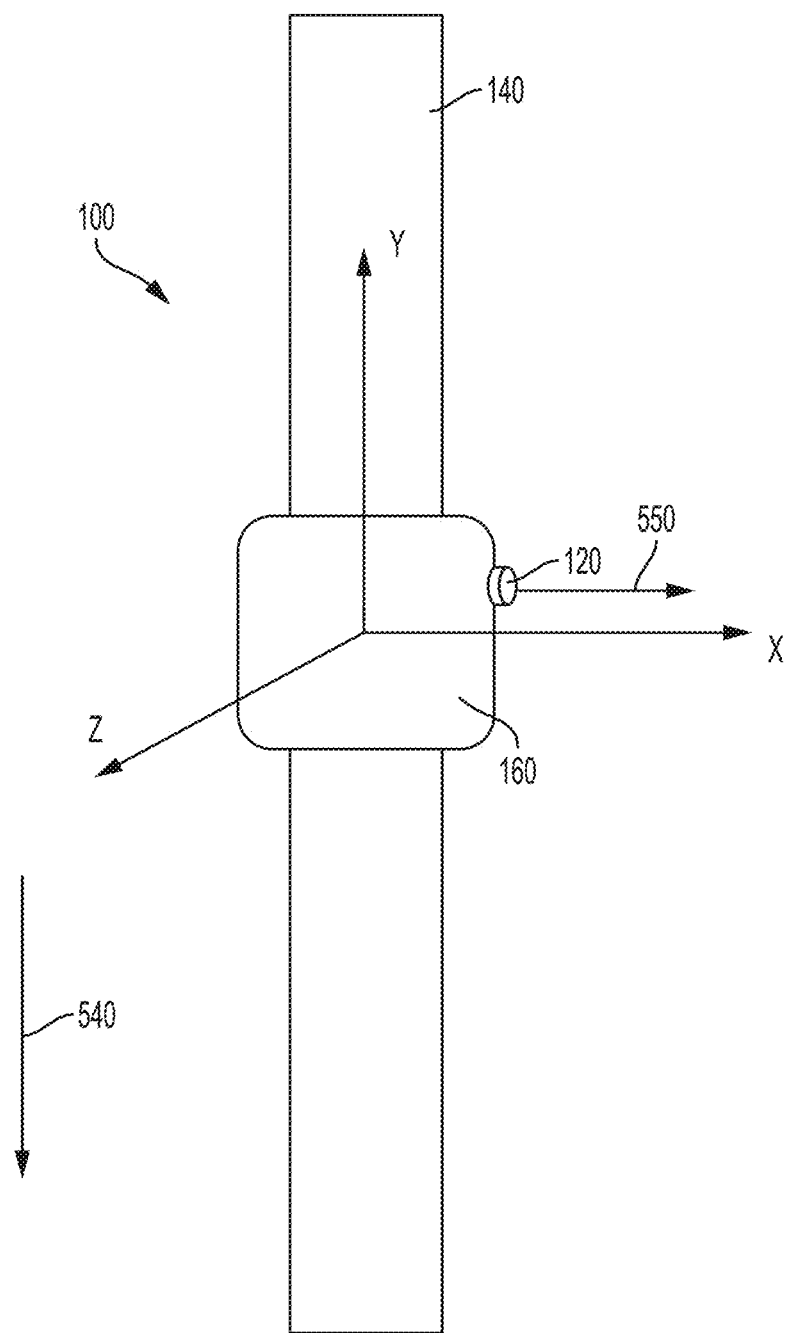
Figure 5D:
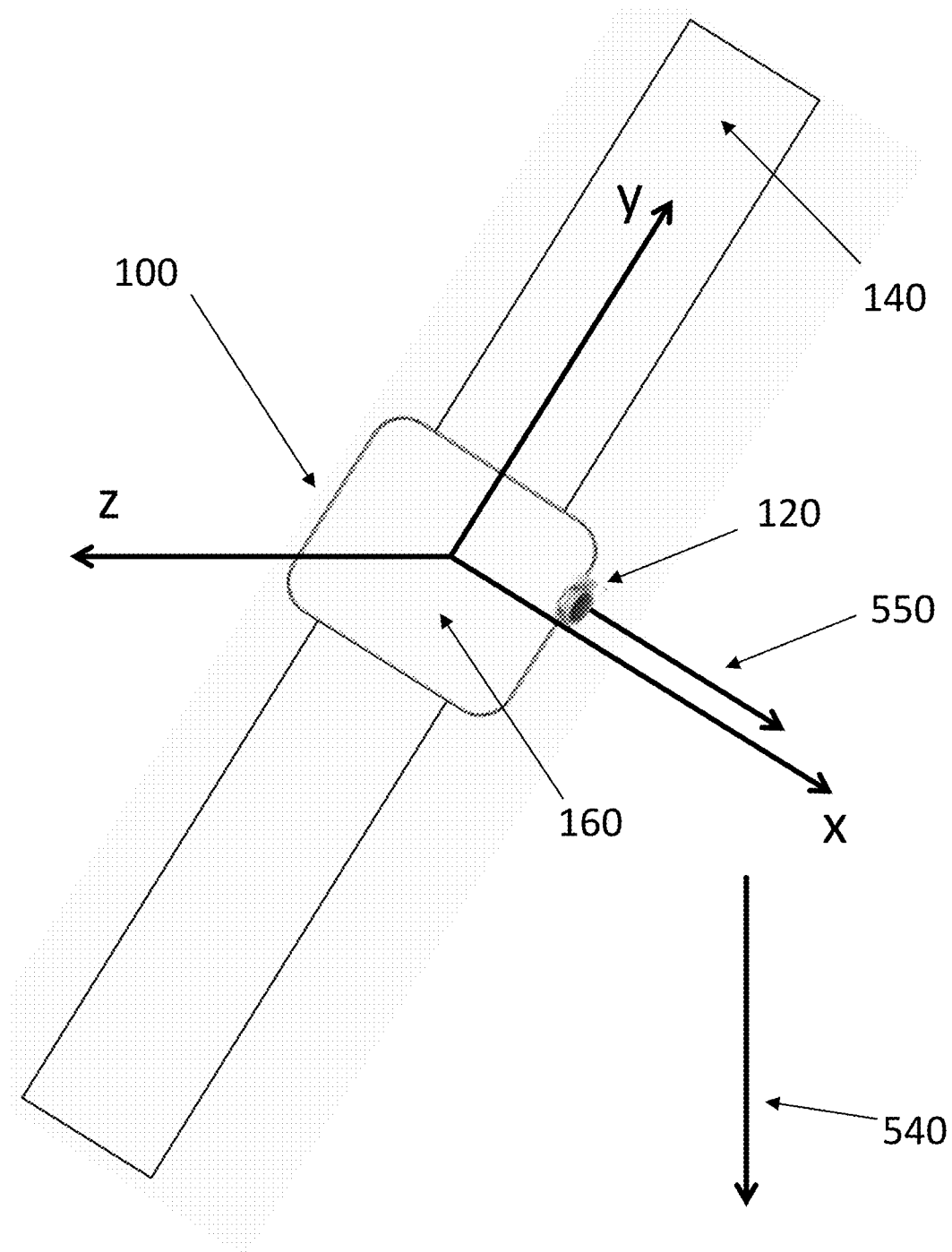

FIG. 5B-5D illustrates examples to express one or more orientations in body-fixed frame of reference 500 according to some embodiments of the present disclosure. In FIG. 5B, an orientation/direction 510 has an angle (φ) 502 with respect to the positive x-axis, an angle (θ) 504 with respect to the positive y-axis, and an angle (ψ) 506 with respect to the positive z-axis. The direction 510 can be expressed in body-fixed frame of reference 500 as [cos(φ), cos(θ), cos(ψ)], which is a non-limiting example/format of the first set of rotational data. For example, direction 520 in FIG. 5B is parallel with and pointing toward the positive x-axis, so the angle (φ) between direction 520 and the positive x-axis is 0 degree; the angle (θ) between direction 520 and the positive y-axis is 90 degrees; and the angle (ψ) between direction 520 and the positive z-axis is 90 degrees. Therefore, direction 520 can be expressed as [cos(0), cos(90), cos(90)], which is [1, 0, 0]. As another example, direction 530 in FIG. 5B is parallel with and pointing toward the positive z-axis, so the angle (φ) between direction 530 and the positive x-axis is 90 degrees; the angle (θ) between direction 530 and the positive y-axis is 90 degrees; and the angle (ψ) between direction 530 and the positive z-axis is 0 degrees. Therefore, direction 530 can be expressed as [cos(90), cos(90), cos(0)], which is [0, 0, 1]. As yet another example, direction 540 represents direction of gravity in FIG. 5B and is parallel with and pointing toward the negative y-axis, so the angle (φ) between direction 540 and the positive x-axis is 90-degrees; the angle (θ) between direction 540 and the positive y-axis is 180 degrees; and the angle (ψ) between direction 540 and the positive z-axis is 90 degrees. Therefore, direction 540 can be expressed as [cos(90), cos(180), cos(90)], which is [0, −1, 0].

In FIG. 5C, wearable device 100 is held vertically. As discussed earlier, the x-axis is parallel with direction pointed by crown 120, the y-axis is parallel with band 140, and the z-axis is perpendicular to display surface 160. Direction 550 in FIG. 5C represents the direction pointed by crown 120, so the angle (φ) between direction 550 and the positive x-axis is 0 degrees; the angle (θ) between direction 550 and the positive y-axis is 90 degrees; and the angle (ψ) between direction 550 and the positive z-axis is 90 degrees. Therefore, direction 550 can be expressed as [cos(0), cos(90), cos(90)], which is [1, 0, 0]. As another example, direction 540 represents direction of gravity in FIG. 5C and is parallel with and pointing toward the negative y-axis, so the angle (φ) between direction 540 and the positive x-axis is 90 degrees; the angle (θ) between direction 540 and the positive y-axis is 180 degrees; and the angle (ψ) between direction 540 and the positive z-axis is 90 degrees. Therefore, direction 540 in FIG. 5C can be expressed as [cos(90), cos(180), cos(90)], which is [0, −1, 0].

In FIG. 5D, wearable device 100 is rotated 45 degrees clockwise compared with FIG. 5C. As discussed earlier, the x-axis is parallel with direction pointed by crown 120, the y-axis is parallel with band 140, and the z-axis is perpendicular to display surface 160. Direction 550 in FIG. 5D represents the direction pointed by crown 120, so the angle (φ) between direction 550 and the positive x-axis is 0 degrees; the angle (θ) between direction 550 and the positive y-axis is 90 degrees; and the angle (ψ) between direction 550 and the positive z-axis is 90 degrees. Therefore, direction 550 can be expressed as [cos(0), cos(90), cos(90)], which is [1, 0, 0]. As another example, direction 540 represents direction of gravity in FIG. 5D. The angle (φ) between direction 540 and the positive x-axis is 45 degrees; the angle (θ) between direction 540 and the positive y-axis is 135 degrees; and the angle (ψ) between direction 540 and the positive z-axis is 90 degrees. Therefore, direction 540 in FIG. 5D can be expressed as [cos(45), cos(135), cos(0)], which is [0.707, −0.707, 0].

It is noted that the expression of direction 550 is the same in FIG. 5C and FIG. 5D even though wearable device 100 has rotated. This is because the body-fixed frame of reference 500 is always fixed with respect to wearable device 100. As a result, when the position of wearable device 100 changes, the three axes in body-fixed frame of reference 500 and direction 550 change too, and the relative position between direction 550 and the three axes remain the same. On the other hand, although the direction of gravity 540 does not change in an "absolute" sense, it does change its position relative to the wearable device 100, when the wearable device 100 changes position. Therefore, the expression of gravity direction 540 does not stay fixed in the body-fixed frame of reference 500 when wearable device changes position.

Figure 6:
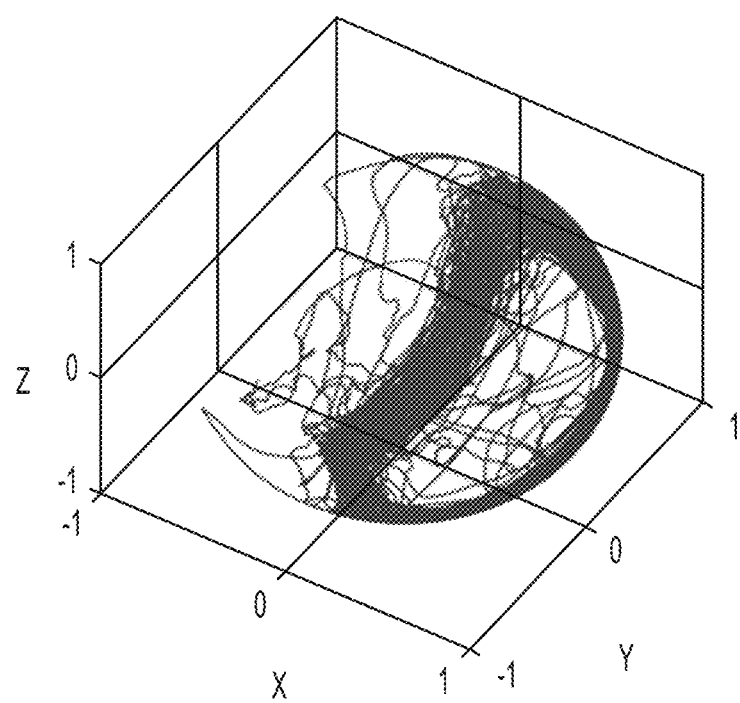
FIG. 6 illustrates a set of rotational data of a wearable device in a body-fixed frame of reference according to some embodiments of the present disclosure.

FIG. 6 illustrates a first set of rotational data of wearable device 100 according to some embodiments of the present disclosure. Specifically, FIG. 6 illustrates estimation of the gravity in the body-fixed frame of reference 500. The x-axis shows cos(φ) where φ is the angle between gravity and the positive x-axis in the body-fixed frame of reference 500. The y-axis shows cos(θ), where θ is the angle between gravity and the positive y-axis in the body-fixed frame of reference 500. The z-axis shows cos(ψ), where ψ is the angle between gravity and the positive z-axis in the body-fixed frame of reference 500. For example, if the display surface of wearable device 100 faces up toward the sky, parallel with the ground, then the gravity direction can be expressed as [0, 0, −1]. As another example, if crown is pointed towards the ground, then the gravity direction can be expressed as [1, 0, 0]. Gravity estimation in body-fixed frame of reference can help indicate when wearable device 100 is making a pitch and/or roll movement. For example, as discussed above, when a user's wrist is in a position such that crown is pointed towards the ground, the gravity direction is [1, 0, 0]. If the user then pitches his or her wrist up for 90 degrees, then display surface of wearable device 100 faces up toward the sky, parallel with the ground, and the gravity direction is expressed as [0, 0, −1]. If the user then rolls his or her wrist up for 90 degrees, then crown of wearable device 100 faces up toward the sky, and the gravity direction is expressed as [−1, 0, 0]. These examples illustrate that gravity direction in the body-fixed frame of reference 500 can change in response to pitch and/or roll movement. In some embodiments, the gravity estimation in body-fixed frame of reference 500 can be used together with accelerometer 260 to estimate gravity. However, the gravity direction in the body-fixed frame of reference 500 does not change in response to yaw movement. For example, if the display surface of wearable device 100 is facing up toward the sky, parallel with the ground, then the gravity direction is expressed as [0, 0, −1.] If the user then makes a yaw movement along the horizontal plane, the gravity direction remains [0, 0, −1].

Also, as discussed above, because wearable device 100 is rotating with the body-fixed frame of reference 500, the directions of wearable device 100 and components thereof are fixed. For example, no matter whether the crown is pointing up, straight, or down, the crown direction is always expressed in a body-fixed frame of reference 500 as [1, 0, 0]. Therefore, in some embodiments, it is more suitable to express the positions of wearable device 100 in a frame of reference that is not body-fixed in order to more readily indicate the movements of wearable device 100 with respect to external references.

At step 430, wearable device 100 converts the first set of rotational data into a second set of rotational data. As described above, rotational data in the body-fixed frame of reference cannot readily indicate whether or not wearable device 100 undergoes movements with respect to external references. To address this issue, wearable device 100 converts the rotational data in the body-fixed frame of reference into rotational data in an inertial frame of reference using techniques appreciated by people skilled in the art such as the one discussed in "Kalman-filter-based orientation determination using inertial/magnetic sensors: observability analysis and performance evaluation," Angelo Maria Sabatini, published Sep. 27, 2011, Sensors 2011, 11, 9182-9206.

Figure 7:
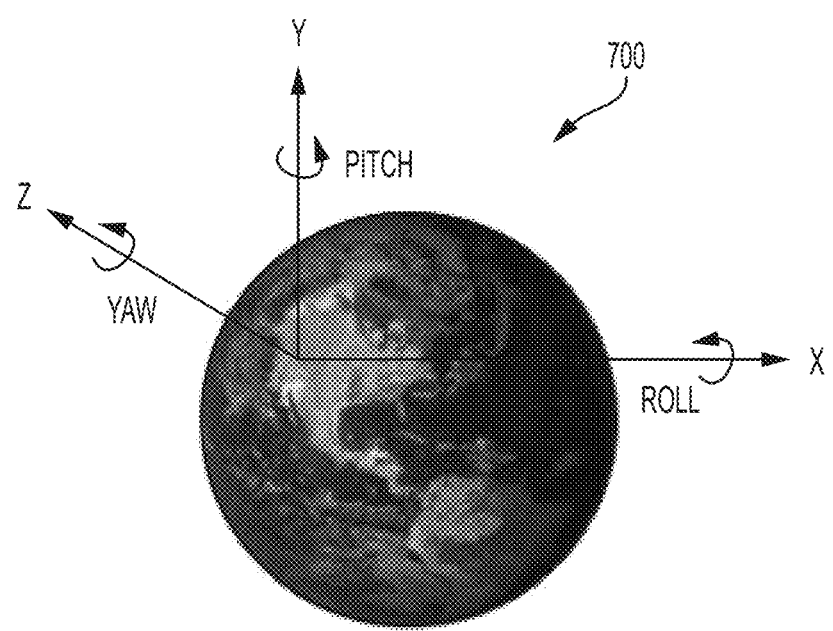
FIG. 7 illustrates an example of an inertial frame of reference according to some embodiments of the present disclosure.

FIG. 7 illustrates an inertial frame of reference 700 according to some embodiments of the present disclosure. In FIG. 7, the z-axis is based on the direction of gravity. The x-axis and the y-axis can be chosen relatively arbitrarily as long as the three axes are perpendicular to each other. The z-axis is also referred to as yaw axis because any yaw movement rotates around the z-axis. In some embodiments, the x-axis can indicate the direction of movements, and the x-axis can be referred to as roll axis because any roll movement rotates around the x-axis. And the y-axis can be referred to as pitch axis because any pitch movement rotates around the y-axis.

Figure 8A:
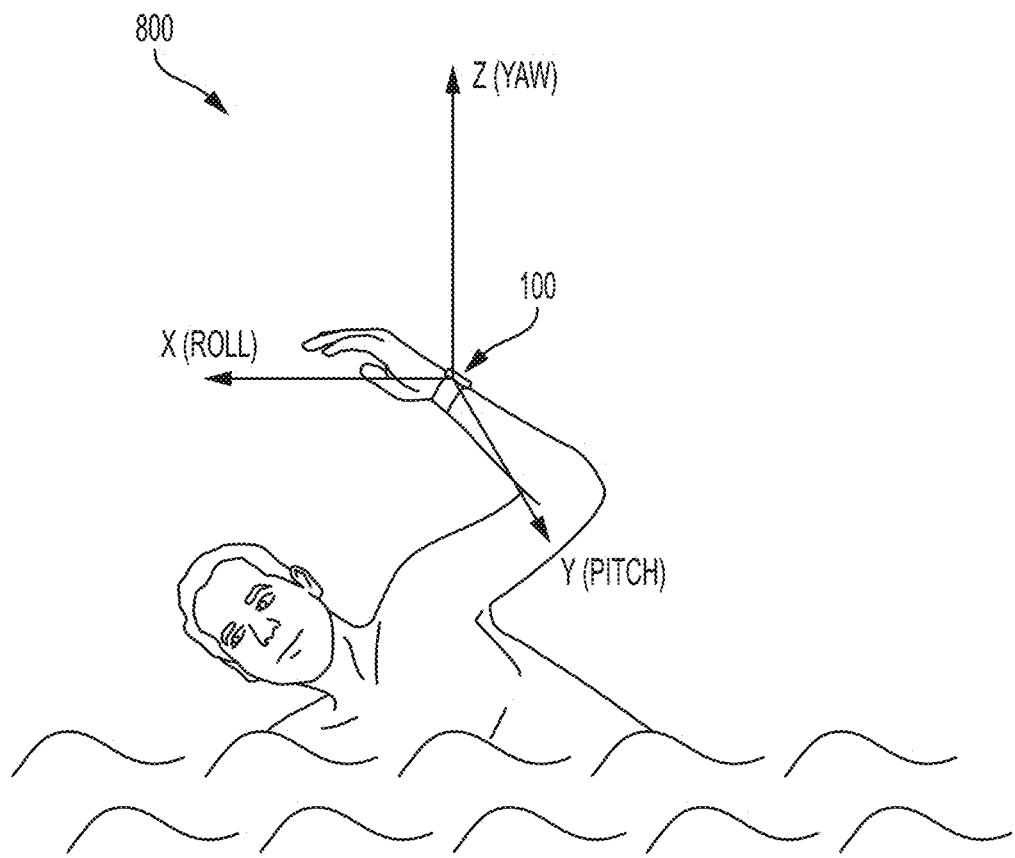
FIGS. 8A-8D illustrate an example of an inertial frame of reference according to some embodiments of the present disclosure.

FIGS. 8A-8D illustrate an example of an inertial frame of reference 800 according to some embodiments of the present disclosure. FIG. 8A depicts inertial frame of reference 800 in a context where a user is swimming. In FIG. 8A, the user wears wearable device 100. But the z-axis (or the yaw axis) in the inertial frame of reference is based on the direction of gravity rather than the wearable device itself. Additionally, assuming the user is swimming laps, the x-axis (or the roll axis) is substantially parallel to the direction of the laps, and the y-axis (or the pitch axis) is perpendicular to the other two axes. In some embodiments, the x-axis (or the roll axis) and the y-axis (or the pitch axis) can be chosen relatively arbitrarily as long as the three axes are perpendicular to each other. In FIG. 8A, the z-axis is also referred to as yaw axis because any yaw movement rotates around the z-axis. Similarly, the x-axis is also referred to as roll axis because any roll movement rotates around the x-axis. And the y-axis is also referred to as pitch axis because any pitch movement rotates around the y-axis. By knowing the difference between the three-axes in the fixed-body frame of reference 500 and the three-axis in the inertial frame of reference 800, the rotational data expressed in the fixed-body frame of reference 500 can be converted into the rotational data expressed in the inertial frame of reference 800 using techniques appreciated by people skilled in the art such as the one discussed in Sabatini.

Figure 8B:
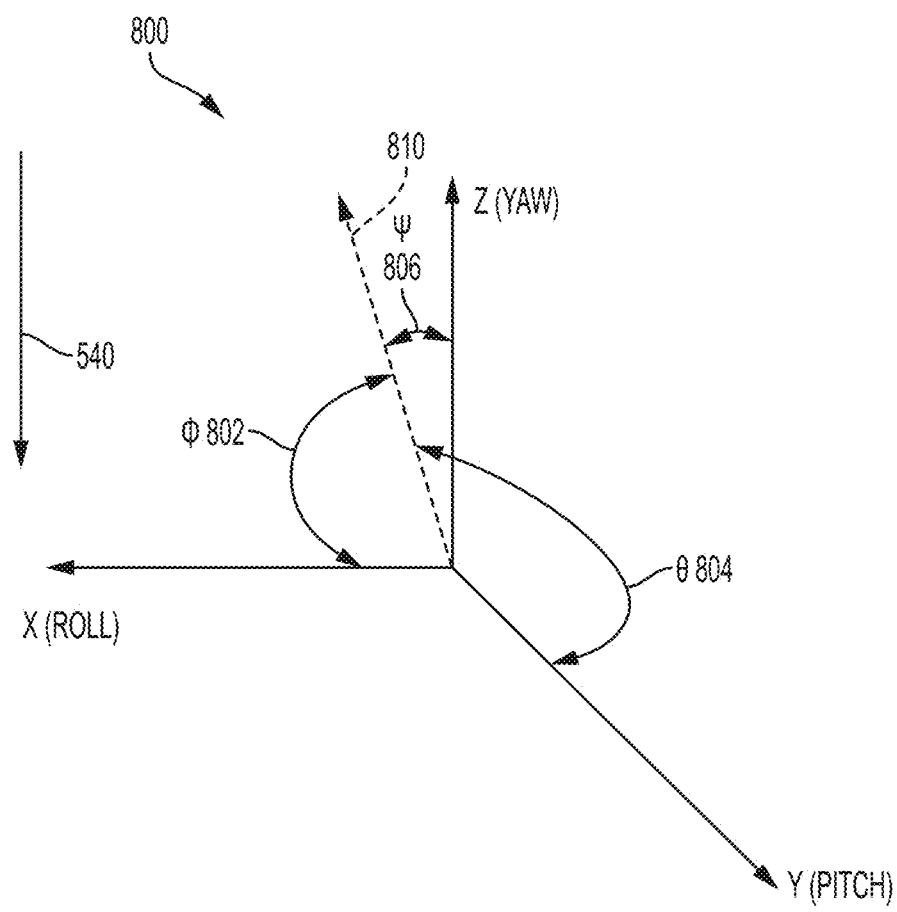

FIG. 8B illustrates that wearable device 100 can make rotational movement with respect to inertial frame of reference 800. In FIG. 8B, an orientation/direction 810 has an angle ($\phi$) 802 with respect to the positive x-axis, an angle ($\theta$) 804 with respect to the positive y-axis, and an angle ($\psi$) 806 with respect to the positive z-axis. The direction 810 can be expressed in inertial frame of reference 800 as [cos($\phi$), cos($\theta$), cos($\psi$)], which is a non-limiting example/format of the second set of rotational data.

Figure 8C:
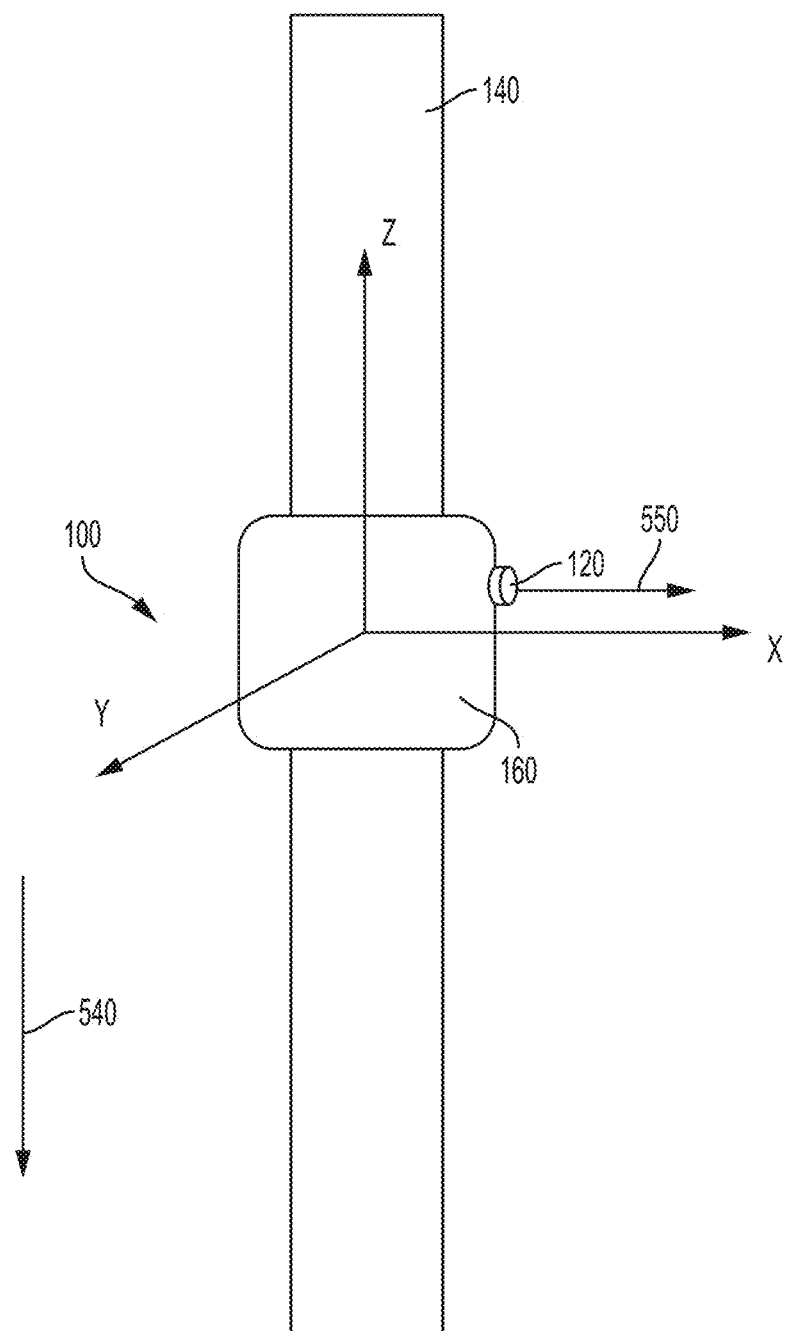
Figure 8D:
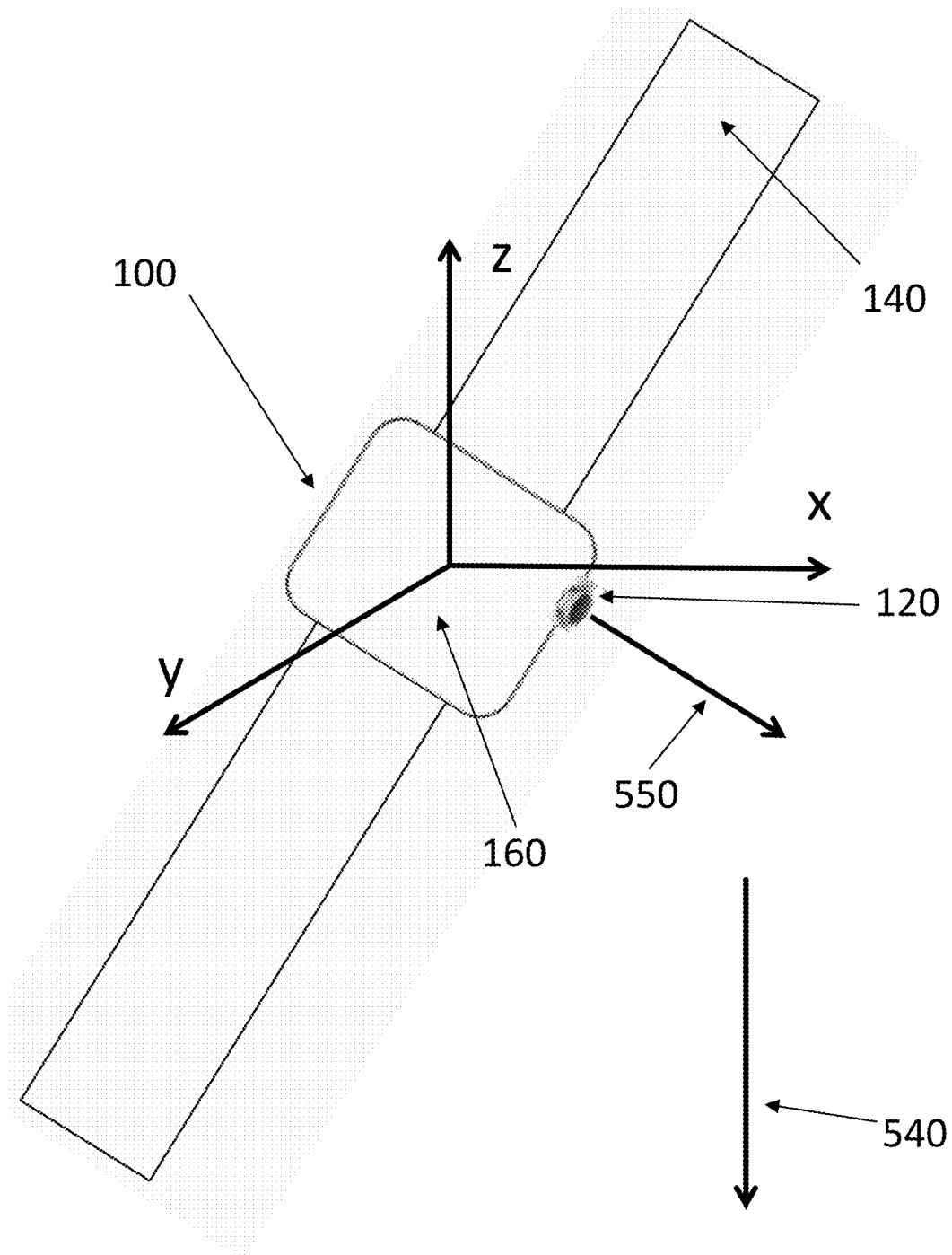

FIGS. 8C and 8D illustrate how same orientations in FIGS. 5C and 5D can be expressed differently in inertial frame of reference 800. In FIG. 8C, wearable device 100 is held vertically, which is the same as FIG. 5C. As discussed earlier, the z-axis is based on the gravity in inertial frame of reference 800. In FIG. 8C, the positive z-axis is chosen as the direct opposite position of gravity, the x-axis is perpendicular to the z-axis and pointing right horizontally, and the y-axis is perpendicular to both x-axis and y-axis and pointing "out" of FIG. 8C. Direction 550 in FIG. 8C represents the direction pointed by crown 120, so the angle ($\phi$) between direction 550 and the positive x-axis is 0 degree; the angle ($\theta$) between direction 550 and the positive y-axis is 90 degrees; and the angle ($\psi$) between direction 550 and the positive z-axis is 90 degrees. Therefore, direction 550 can be expressed as [cos(0), cos(90), cos(90)], which is [1, 0, 0]. As another example, direction 540 represents direction of gravity in FIG. 8C and is parallel with and pointing toward the negative z-axis, so the angle ($\phi$) between direction 540 and the positive x-axis is 90 degrees; the angle ($\theta$) between direction 540 and the positive y-axis is 90 degrees; and the angle ($\psi$) between direction 540 and the positive z-axis is 180 degrees. Therefore, direction 540 in FIG. 8C can be expressed as [cos(90), cos(90), cos(180)], which is [0, 0, −1].

In FIG. 8D, wearable device 100 is rotated 45 degrees clockwise compared with FIG. 8C. Because the three axes are based on gravity, they can remain the same as FIG. 8C. Direction 550 in FIG. 8D represents the direction pointed by crown 120, and the angle ($\phi$) between direction 550 and the positive x-axis is 45 degrees; the angle ($\theta$) between direction 550 and the positive y-axis is 90 degree; and the angle ($\psi$) between direction 550 and the positive z-axis is 135 degree. Therefore, direction 550 can be expressed as [cos(45), cos(90), cos(135)], which is [0.707, 0, −0.707]. As another example, direction 540 represents direction of gravity in FIG. 8D. The angle ($\phi$) between direction 540 and the positive x-axis is 90 degree; the angle ($\theta$) between direction 540 and the positive y-axis is 90 degrees; and the angle ($\psi$) between direction 540 and the positive z-axis is 180 degrees. Therefore, direction 540 in FIG. 8D can be expressed as [cos(90), cos(90), cos(180)], which is [0, 0, −1].

It is noted that the expression of gravity direction 540 is the same in FIG. 8C and FIG. 8D even though wearable device 100 has rotated. This is because the inertial frame of reference 800 is always fixed with respect to gravity. As a result, when position of wearable device 100 changes, the three axes in the inertial frame of reference 800 do not move. On the other hand, the direction 550 does move with respect to the three axes, so the expression of direction 550 can change in the inertial frame of reference 500 even though it is fixed in body-fixed frame of reference 500.

Figure 9:
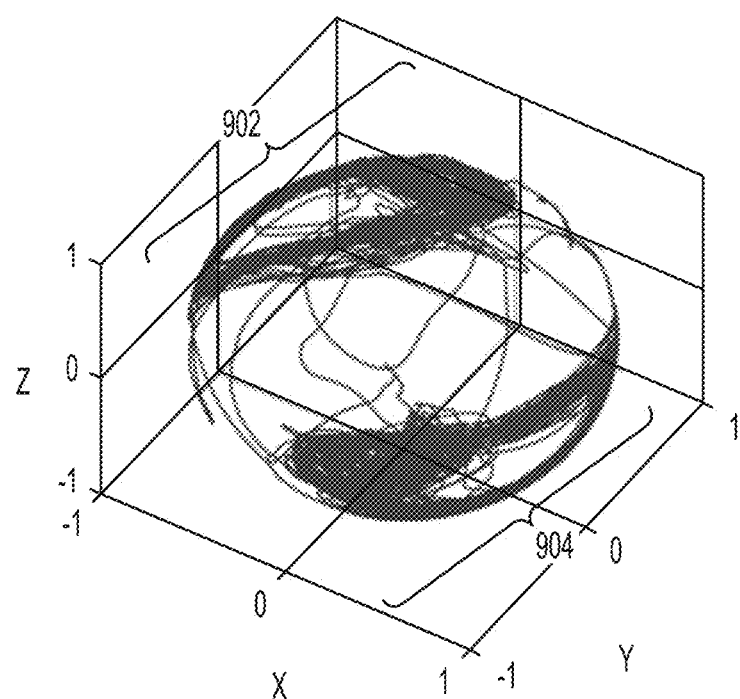
FIG. 9 illustrates a set of rotational data of a wearable device in an inertial frame of reference according to some embodiments of the present disclosure.

FIG. 9 illustrates a first set of rotational data of wearable device 100 according to some embodiments of the present disclosure. Specifically, FIG. 9 illustrates estimation of crown direction in the inertial frame of reference 800 while a user is swimming laps. The x-axis shows cos($\phi$) where $\phi$ is the angle between crown direction and the positive x-axis in the inertial frame of reference 800. The y-axis shows cos($\theta$), where $\theta$ is the angle between crown direction and the positive y-axis in the inertial frame of reference 800. The z-axis shows cos($\psi$), where w is the angle between crown direction and the positive z-axis in the inertial frame of reference 800. For example, if the display surface of the wearable device 100 is facing up towards the sky, parallel with the ground, and the crown is pointed towards the positive x-axis, then the crown direction can be expressed as [1, 0, 0]. Further, if wearable device 100 is making yaw movements, and the crown changes direction to point towards the negative x-axis, then the crown direction can be expressed as [−1, 0, 0]. As another example, if the crown is pointed towards the ground, then the new crown direction can be expressed as [0, 0, 1]. The rotational data in FIG. 9 are largely divided into two clusters, 902 and 904, because every time the user makes a turn, the angle $\phi$ between crown direction and the positive x-axis in the inertial frame of reference 800 changes substantially around 180 degrees. Therefore, the rotational data expressed in FIG. 9 (i.e., the data switching from cluster 902 to cluster 904, or vice versa) can indicate that wearable device 200 is undergoing a steady-state change in the direction that the user is heading.

The present disclosure describes ways to estimate energy expenditure of a user while swimming. Generally, a user's energy expenditure while swimming can depend on one or more of the following factors: swimming style, skill level, stroke rate, stroke length, gender, body surface area, and/or body composition and distribution. In some embodiments, other relevant factors can also affect the user's energy expenditure.

Figure 10:
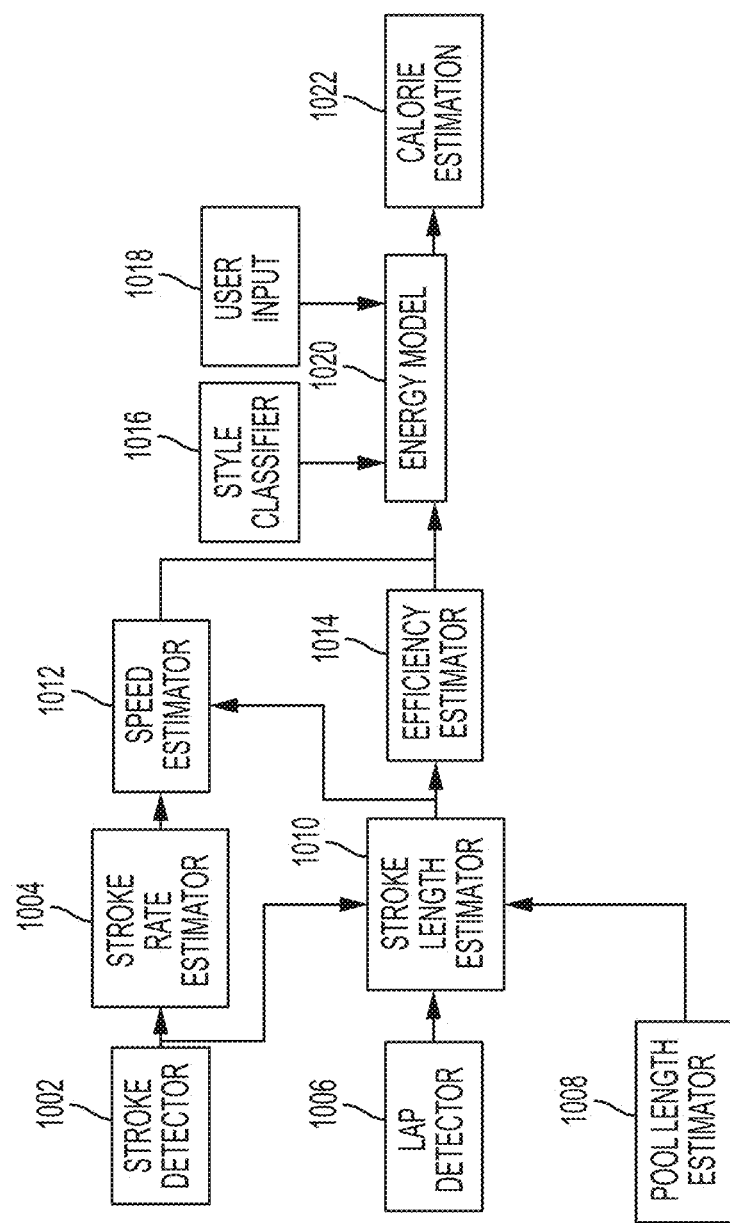
FIG. 10 illustrates a method of estimating energy expenditure of a user while swimming according to some embodiments of the present disclosure.

FIG. 10 illustrates a flow chart illustrating a computerized process 1000 of determining a user's energy expenditure while swimming according to certain embodiments of the present disclosure. In some embodiments, the computerized process 1000 can be modified by, for example, having steps combined, divided, rearranged, changed, added, and/or removed.

At step 1002, wearable device 100 may detect each time the user makes a stroke. In some embodiments, wearable device 100 can only detect the strokes made by the arm wearing the wearable device 100. In these embodiments, for every stroke detected, the user may make two strokes, and the metrics related to strokes can sometimes be adjusted accordingly.

At step 1004, wearable device 100 may estimate stroke rate of the user. In some embodiments, the stroke rate is determined as the number of strokes per unit period, such as a minute. For example, if wearable device 100 detects 120 strokes in four minutes, then the stroke rate can be determined to be 120 strokes/4 minutes=30 stroke/min.

At step 1006, wearable device 100 may detect each time the user finishes a lap.

At step 1008, wearable device 100 may determine the length of the pool where the user swims, as described in co-pending U.S. patent application Ser. No. 15/691,245, titled "Systems and methods for determining swimming metrics", which is incorporated by reference herein by its entirety.

At step 1010, wearable device 100 may estimate stroke length of the user. In some embodiments, the stroke length is determined as the length per stroke. For example, if wearable device 100 detects that the user finishes four laps with each lap 50 meters, and wearable device 100 detects the user makes 100 strokes in the four laps, then wearable device 100 can determine the stroke length as 50 meters/lap*4 laps/100 strokes=2 meter/stroke.

At step 1012, wearable device 100 may estimate the speed of the user. In some embodiments, wearable device 100 estimates the speed of the user based on the user's stroke rate and stroke length. The user's speed can be determined as stroke rate*stroke length. For example, if wearable device 100 detects that the user finishes four laps with each lap 50 meters in five minutes, and wearable device 100 detects that the user makes 100 strokes in the four laps, then as described above, wearable device 100 can determine the stroke length as 50 meters/lap*4 laps/100 strokes=2 meter/stroke and the stroke rate as 100 strokes/4 minutes=25 stroke/min. Then the speed can be determined as stroke length*stroke rate=2 meter/stroke*25 strokes/min=50 meter/min. In some embodiments, the speed of the user can also be determined by one or more sensors of wearable device 100.

At step 1014, wearable device 100 may estimate the user's efficiency. In some embodiments, wearable device 100 estimates the user's efficiency based on two factors. One factor is the user's stroke length. In general, the longer the user's stroke length, the higher the user's efficiency. Another factor is the user's stroke orbit consistency. In general, high stroke orbit consistency indicates high efficiency. Systems and methods for determining stroke orbit consistency are described in co-pending U.S. patent application Ser. No. 15/692,726 titled "Systems and methods of swimming analysis", which is incorporated by reference herein in its entirety.

At step 1016, wearable device 100 may classify the user's swimming style. In some embodiments, wearable device 100 can classify the user's swimming style as one of the following styles: breaststroke, backstroke, freestyle, butterfly, or unknown. Systems and methods for classifying swimming strokes are also described in co-pending U.S. patent application Ser. No. 15/692,726 titled "Systems and methods of swimming analysis", which is incorporated by reference herein in its entirety.

At step 1018, wearable device 100 may receive one or more inputs from the user. In some embodiments, wearable device 100 can receive user's gender. In some cases, female users can have more body fat than male users. Users with more body fat are more buoyant and as a result expend less energy. In some embodiments, wearable device 100 can receive other information regarding the user, such as the user's height and weight. In some embodiments, wearable device 100 can calculate the user's body mass index based on the user's height and weight, which measures a user's body fat and can be used to calculate a swimmer's buoyancy and energy expenditure.

At step 1020, wearable device 100 may select an energy expenditure model based on information provided in step 1016 and/or step 1018. For example, if wearable device 100 determines the user is swimming in freestyle, it will choose a model corresponding to freestyle. In some embodiments, once wearable device 100 selects an energy expenditure model based on the user's swimming style, it can further modify the model based on the gender.

At step 1022, wearable device 100 may estimate the user's energy expenditure based on the user's speed, efficiency, and the selected model. In some embodiments, the user's energy expenditure can be expressed as the metabolic equivalent of task (MET). MET has unit of kcal/(kg*h), and 1 MET indicates the rate of energy spent per unit surface of a person during sitting.

Figure 11:
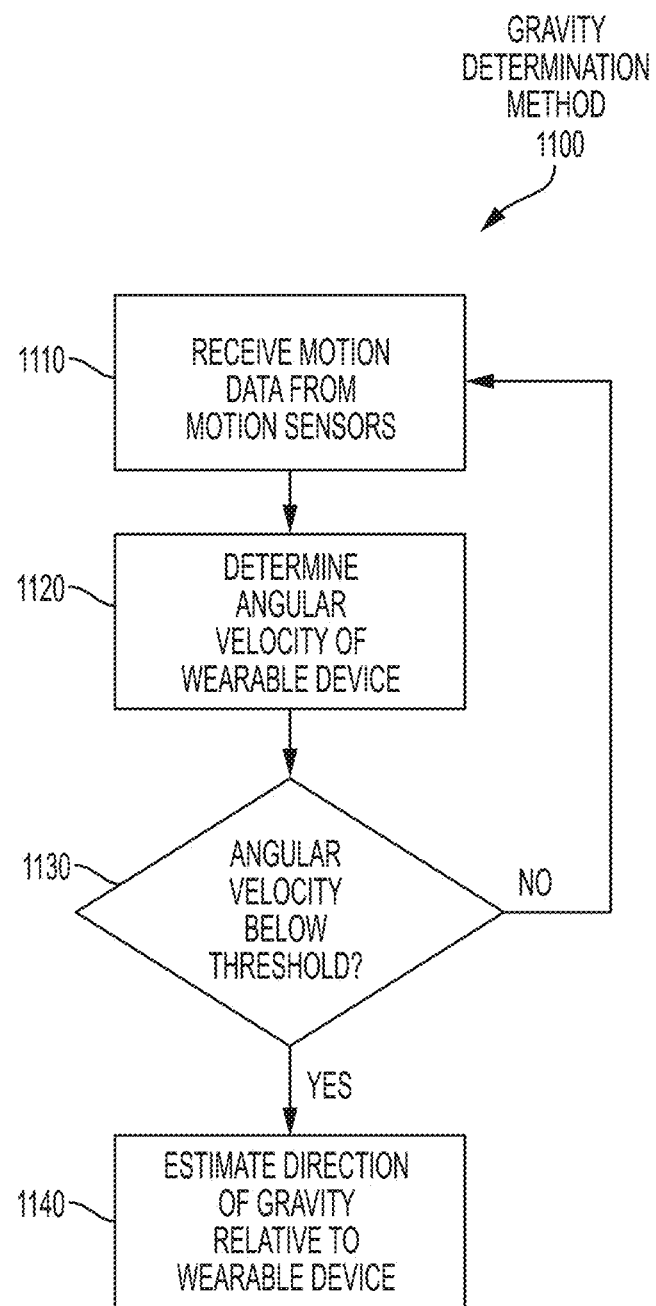
FIG. 11 illustrates a method of determining a direction of gravity according to some embodiments of the present disclosure.

FIG. 11 shows a method 1100 for determining a direction of gravity according to some embodiments of the present disclosure. The determined direction of gravity may be used to determine a frame of reference for motion information, such as rotational data, of wearable device 100. In some embodiments, method 1100 can be modified by, for example, having steps combined, divided, rearranged, changed, added, and/or removed. Gravity determination method 1100 may begin at step 1110

At step 1110, wearable device 100 may receive motion information from the one or more motion sensors 240 on a wearable device (e.g., wearable device 100) of a user. In some embodiments, motion information may include three-dimensional rotational information from one or more sensors 240 such as gyroscope 250 and three-dimensional acceleration information from one or more sensors 240 such as accelerometer 260. In some embodiments, motion information may be filtered such as by a low-pass filter to remove unwanted noise from the ambient.

At step 1120, wearable device 100 may determine the angular velocity of wearable device 100 with respect to a frame of reference such as a body-fixed frame of reference or an inertial frame of reference.

At step 1130, wearable device 100 may determine whether the angular velocity of wearable device 100 determined at step 1120 is below a threshold. For example, the threshold may be approximately 0.05 radians per second, 0.2 radians per second, or 0.5 radians per second, etc. If the angular velocity exceeds the threshold (e.g., when the user is doing exercise), wearable device 100 may return to step 510. In some embodiments, wearable device 100 may pause or wait for a period of time (e.g., 1 second, 5 seconds, 1 minute, etc.) before proceeding at step 1110.

If the angular velocity is below the threshold (e.g., when the user is relatively still), wearable device 100 may proceed to step 1140. In some embodiments, at step 1130 wearable device 100 may determine if the magnitude of forces acting on wearable device 100 are approximately equal to the normal force of gravity (1G) before proceeding to step 1140. If the magnitude is not approximately the normal magnitude, wearable device 100 may also return to block 1110. Wearable device 100 may estimate the direction of gravity when the angular velocity is below the threshold (e.g., when the user is relatively still) to avoid or reduce interference of confusion from acceleration due to other movements. Hypothetically, if wearable device 100 is having a 1 g acceleration along x-axis, then wearable device 100 may incorrectly determine the direction of gravity.

At step 1140, wearable device 100 may estimate the direction of gravity relative to wearable device 100. For example, in some embodiments, when wearable device 100 is held relatively still, accelerometer 260 within wearable device 100 may provide data about the direction of forces acting on wearable device 100, which may be attributable primarily to gravity. In some embodiments, wearable device 100 may determine whether the user wearing wearable device 100 is accelerating (e.g., speeding up or slowing down) or traveling at an approximately constant velocity so as to further improve the estimate of the direction of gravity.

In some embodiments, wearable device 100 may end gravity determination method 1100 after outputting the estimated direction of gravity. In other embodiments, wearable device 100 may return to step 1110 to refine or otherwise repeat the method of estimating the direction of gravity relative to the wearable device.

Figure 12:
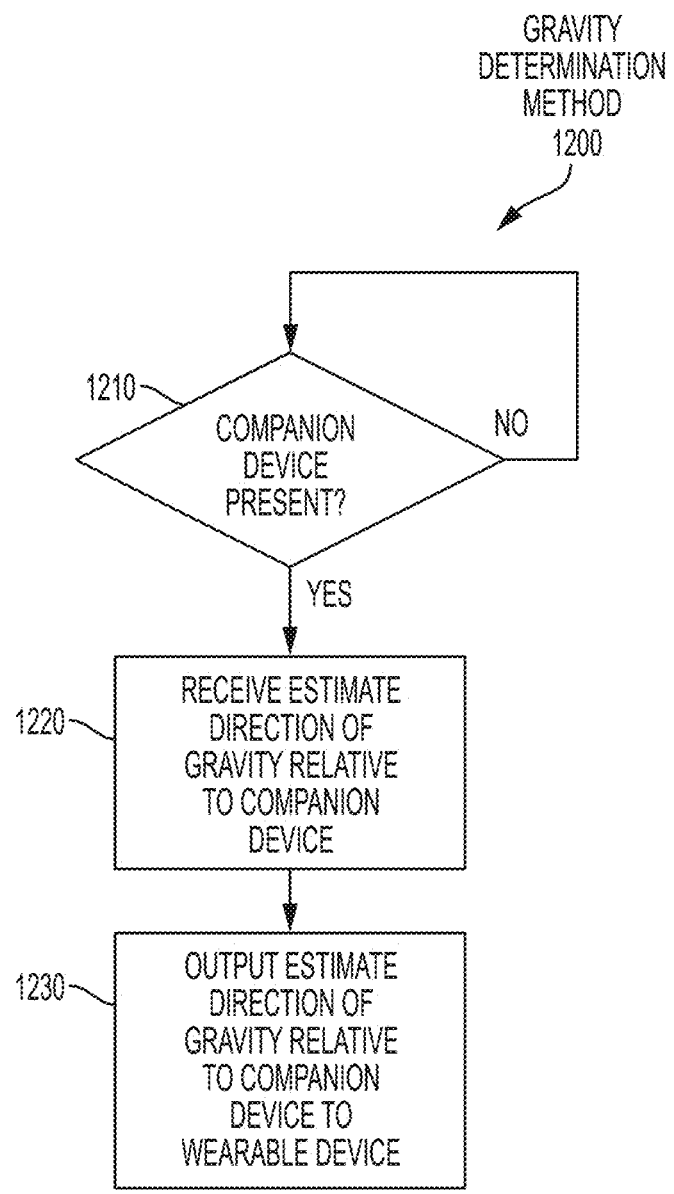
FIG. 12 illustrates a method of determining a direction of gravity according to some embodiments of the present disclosure.

FIG. 12 shows a method 1200 for determining a direction of gravity according to some embodiments of the present disclosure. In some embodiments, the method 1200 can be modified by, for example, having steps combined, divided, rearranged, changed, added, and/or removed. Gravity determination method 1200 can be used when the user has companion device 300 and may begin at step 1210.

At step 1210, wearable device 100 may periodically or continuously check for the presence of a companion device (e.g., companion device 300). For example, in some embodiments, wearable device 100 may determine whether a connection (e.g., Bluetooth, IEEE 802.11 Wi-Fi, or other wireless or wired communication channel) has been established or may be established with companion device 300. If the companion device 300 is present, wearable device 100 and/or companion device 300 may proceed to step 1220.

At step 1220, wearable device 100 and/or companion device 300 may estimate the direction of gravity relative to companion device 300. In some embodiments, in contrast to the gravity determination method 1100, it may not be necessary to check whether the angular velocity of companion device 300 is below a threshold because most or all of rotation of the angular velocity of companion device 300 may be orthogonal to the direction of gravity.

At step 1230, wearable device 100 and/or companion device 300 may output the direction of gravity relative to companion device 300. In some embodiments, the direction of gravity relative to companion device 300 may be combined or otherwise compared with the direction of gravity relative to wearable device 100. In some embodiments, companion device 300 may further determine a rotation rate around the direction of gravity relative to the companion device and output the rotation rate instead of or in addition to the direction of gravity relative to companion device 300.

In some embodiments, wearable device 100 and/or companion device 300 may end gravity determination method 1200 after outputting the estimated direction of gravity. In other embodiments, wearable device 100 and/or companion device 300 may return to step 1210 to refine or otherwise repeat the method of estimating the direction of gravity relative to the wearable device.

In some embodiment, the process 1000 also considers anaerobic contribution when estimating the user's overall energy expenditure. During high intensity workouts such as swimming, the anaerobic component plays an important role in the total energy expenditure.

Figure 13:
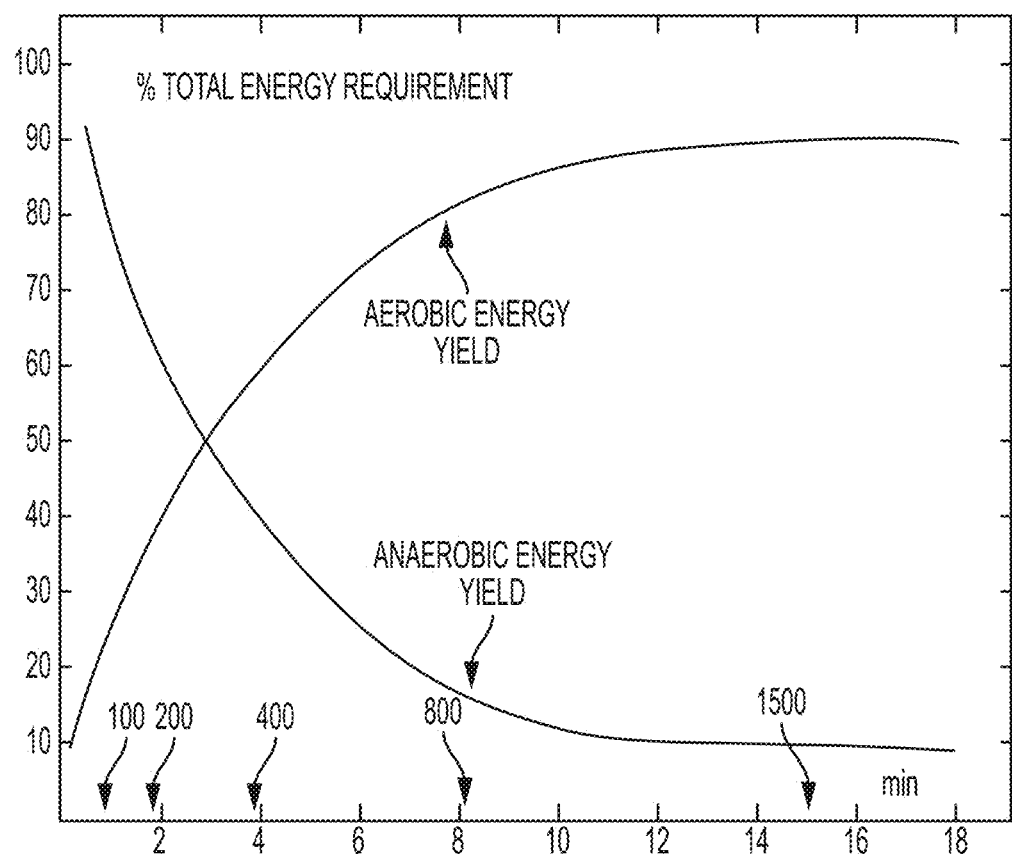
FIG. 13 illustrates percentage of aerobic and anaerobic contributions to user's total energy expenditure while swimming according to some prior published research.

For example, FIG. 13 illustrates percentage of aerobic and anaerobic contributions to user's total energy expenditure while swimming according to some prior published research. FIG. 13 is adapted from data by Hermansen and Karlsson (1967) and Houston (1978). In FIG. 13, the x-axis shows the duration of the swimming workout expressed in minutes, and the y-axis shows the percentage of total energy expenditure. FIG. 13 shows that when the user swims for a short time (e.g., less than four minutes), the anaerobic contribution to energy expenditure is more dominant. And when the user swims for a longer time, the aerobic component becomes more dominant.

Figure 14:
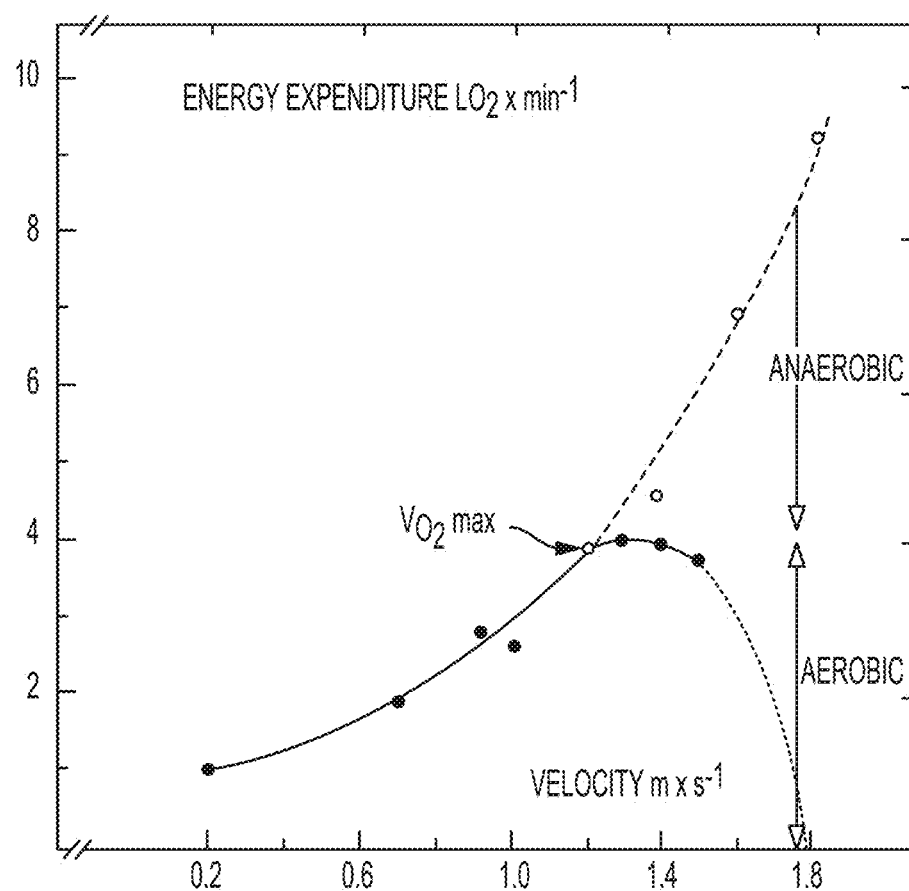
FIG. 14 illustrates a user's energy expenditure as a function of swimming speed according to some prior published research.

As another example, FIG. 14 illustrates a user's energy expenditure as a function of swimming speed according to some prior published research. FIG. 14 is adapted from Pendergast et al. (1978b). In FIG. 14, the x-axis shows swimming speed, and the y-axis shows energy expenditure. The solid line and solid dots show the aerobic contribution to energy expenditure, and the dashed line and open dots show the anaerobic contribution to energy expenditure. FIG. 14 shows that when the user swims at a lower speed (e.g., less than 1.2 m/s), the aerobic component is more dominant. And when the user swims at a higher speed, the anaerobic component is more dominant.

Both FIG. 13 and FIG. 14 show that, in some cases, ignoring the anaerobic component could lead to inconsistent user experience and incorrect/underestimated calorie values.

There are several ways to modify the model shown in FIG. 10 to consider the anaerobic component of the user's energy expenditure. In some embodiments, the user's anaerobic energy expenditure can be estimated based on the user's fraction of heart rate reserve (FHR). FHR may be defined as the ratio of how close an individual's current heart rate is to his or her maximum heart rate (e.g., HRmax−HR) to the individual's heart rate range (e.g., HRmax−HRmin):

$$FHR=(HRmax-HR)/(HRmax-HRmin) \quad (Eq. 1)$$

FHR may range from 0 to 1 for any individual. When an individual's FHR is close to 0, it indicates that the user's heart rate is close to the individual's maximum heart rate. Similarly, when an individual's FHR is close to 1, it indicates that the individual's heart rate is close to the individual's minimum heart rate.

Figure 15:
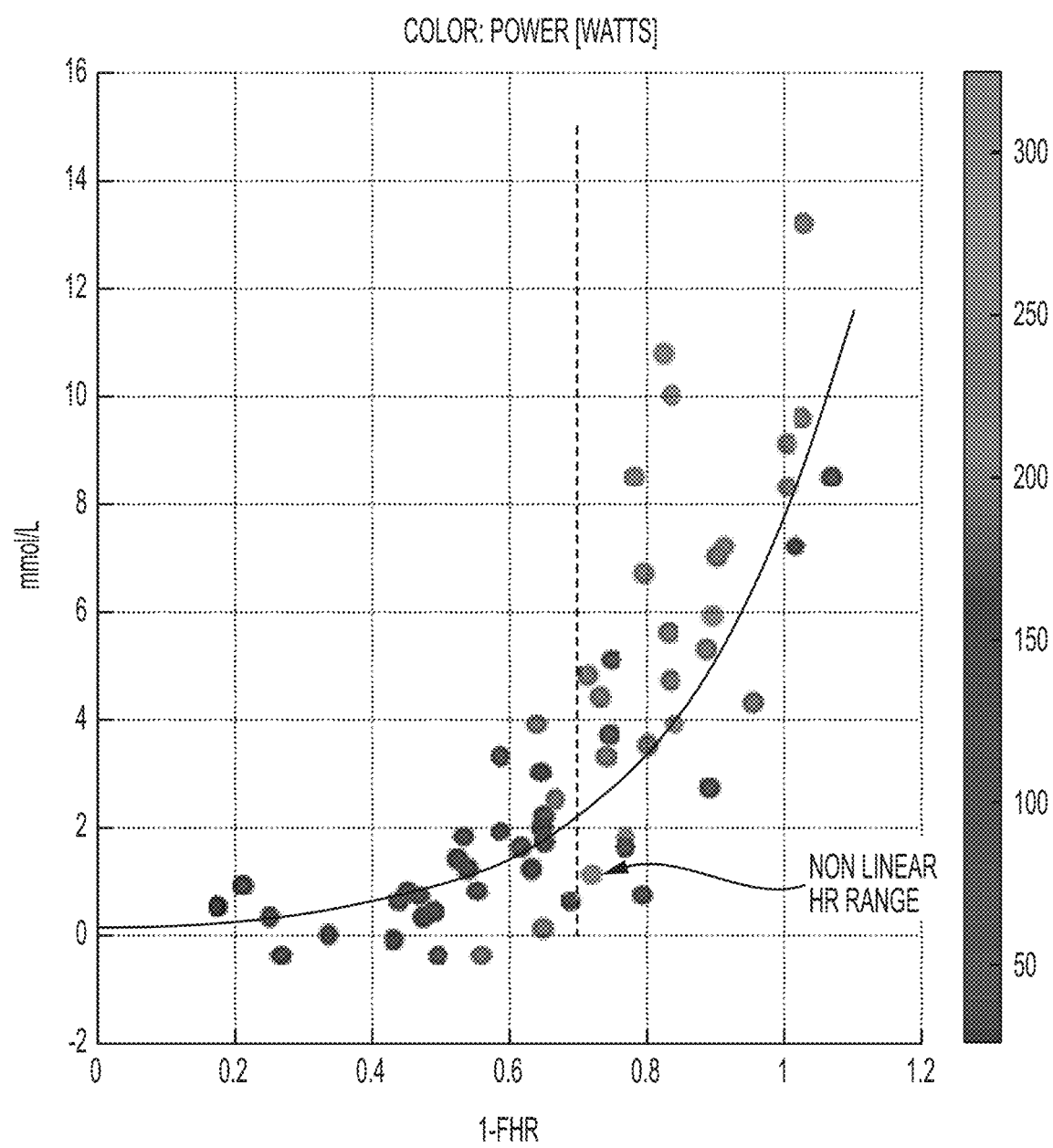
FIG. 15 illustrates the relationship between the user's lactate concentration and the user's FHR according to some embodiments of the present disclosure.

For example, FIG. 15 illustrates the relationship between the user's lactate concentration and the user's FHR according to some embodiments of the present disclosure. The x-axis shows the value of 1−FHR, and the y-axis shows the user's lactate concentration. FIG. 15 shows when the value of 1−FHR is greater than 0.7, the user's lactate concentration increases much faster. Because one's lactate concentration is positively related to one's anaerobic energy expenditure, when the value of 1−FHR is greater than 0.7, the user's anaerobic energy expenditure is more pronounced. When 1−FHR is greater than 0.7, FHR is less than 0.3, which means the user's heart rate is relatively close to his or her maximum heart rate. Therefore, in some embodiments, wearable device 100 can monitor the user's heart rate, and increase the estimation of energy expenditure in process 1000 to take the anaerobic contribution to energy expenditure into consideration based on the user's heart rate.

In some embodiments, wearable device 100 can estimate the user's anaerobic energy expenditure based one or more of the following factors about the user: stroke length, stroke rate, and/or speed.

Figure 16:
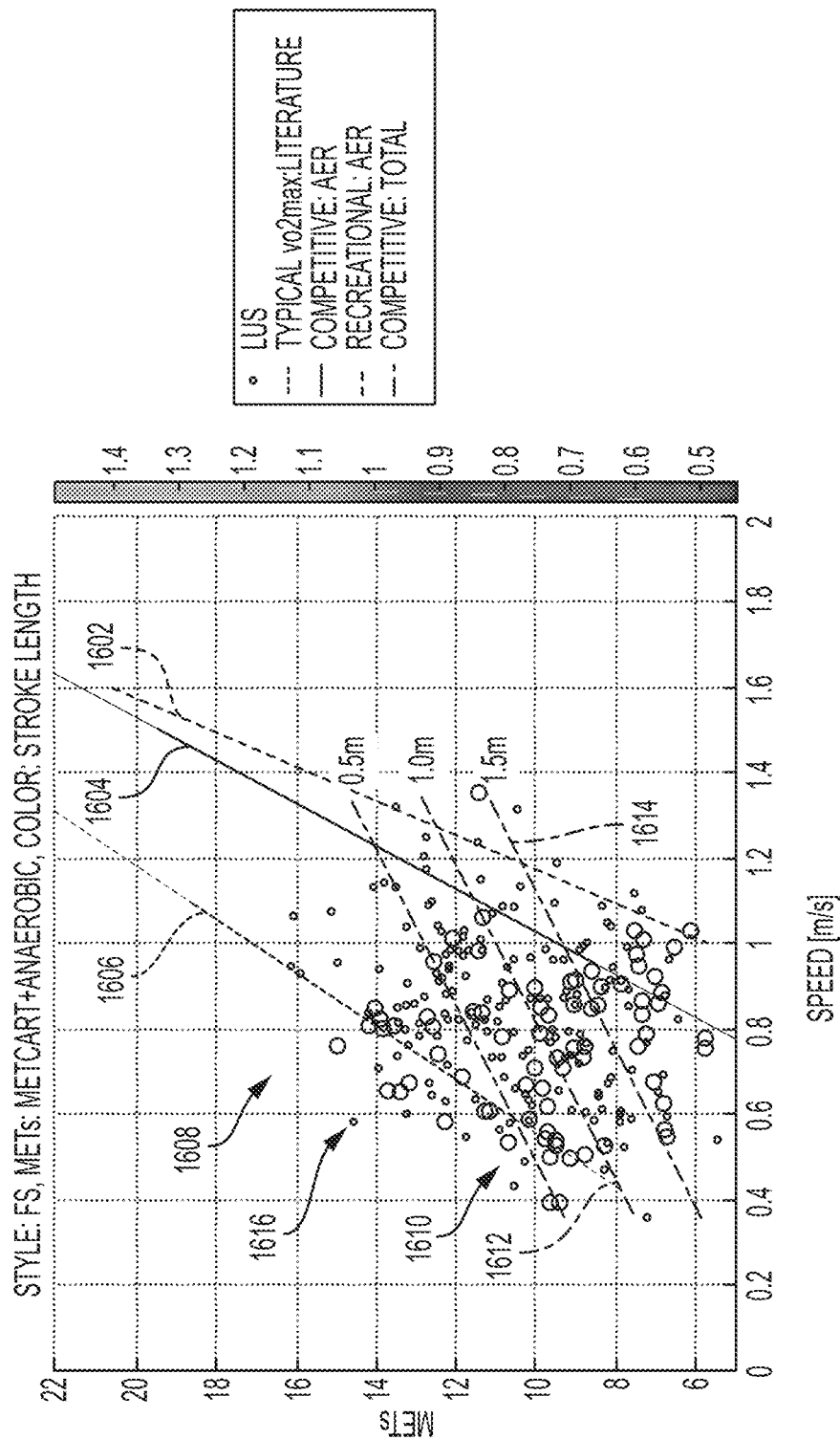
FIG. 16 shows plot of total metabolic equivalent of task (METs) vs. speed, according to some embodiments of the present disclosure.

FIG. 16 shows plot of total METs versus speed, according to some embodiments of the present disclosure. In FIG. 16, the x-axis is the user's swimming speed in freestyle, and the y-axis is the user's METs estimated by the model shown in FIG. 10. In FIG. 16, each circle represents a sample. For example, circle 1616 represents a user with speed at around 0.6 m/s with stroke length around 1 m, and the estimated MET is around 14.8. FIG. 16 also plots some previously published research by others. For example, curve 1602 shows total METs versus speed for competitive swimmers, curve 1604 shows aerobic METs versus speed for competitive swimmers, curve 1606 shows total METs versus speed for recreational swimmers. FIG. 16 also shows regression models based on stroke length for all samples. For example, curve 1610 shows total METs versus speed estimated for a swimmer with stroke length of 0.5 m, curve 1610 shows total METs versus speed estimated for a swimmer with stroke length of 1.0 m, and curve 1610 shows total METs versus speed estimated for a swimmer with stroke length of 1.5 m. FIG. 16 shows that, in some embodiments, based on the user's speed, stroke length, and swimming style, wearable device 100 can estimate the user's energy expenditure such as METs.

While many swimmers swim in pools, swimmers competing in open water events or in triathlons often swim in open waters, for example, lakes, oceans and rivers. In these open environments, calculating energy expenditure for a particular swimming workout can be challenging. For example, because laps are not being counted in a set distance pool, distance estimates may be difficult. Even with the assistance of a global positioning system (GPS) it may be difficult to obtain an accurate GPS fix. Further, open water conditions result in unknown resistance to the swimmer, for example water currents, waves, and even varying water densities.

Figure 17:
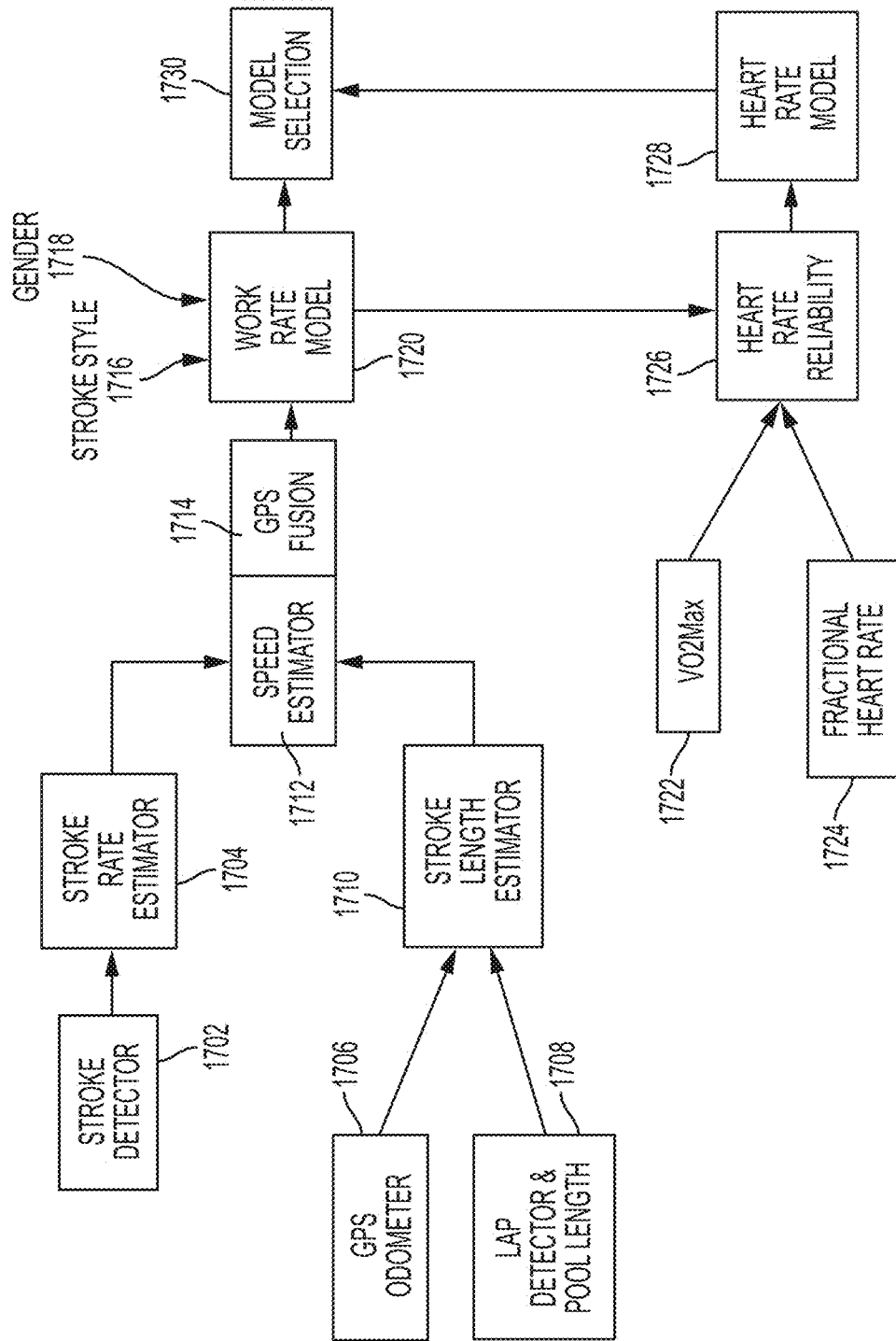
FIG. 17 illustrates a method of estimating energy expenditure of a user in open water according to some embodiments of the present disclosure.

FIG. 17 illustrates a method of estimating energy expenditure of a user in open water according to some embodiments of the present disclosure. FIG. 17 is substantially similar to FIG. 10 above. However, FIG. 17 has the additional components/steps related to heart rate measurements and calculations: GPS odometer 1706, GPS sensor fusion 1714, VO$_2$max 1722, fractional heart rate 1724, heart rate reliability 1726 and heart rate model 1728.

For example, in some embodiments, a GPS sensor can be used to improve the stroke length estimates from 1710 and also the speed calculations from 1712. Accordingly, a more accurate work rate model for the swimming session can be created.

In some embodiments, data from a PPG heart rate sensor can also be used to provide a more accurate calorie determination. For example, as discussed in the co-pending U.S. patent application Ser. No. 15/466,397, titled "Techniques for Jointly Calibrating Load and Aerobic Capacity," the user's VO2max 1722 and fractional heart rate 1724 can be determined. Based on the user's VO2max 1722 and fractional heart rate 1724 and the work rate model 1720, a heart rate reliability 1726 and then a heart rate can be determined. In some embodiments, heart rate measurements can be more reliable in segments with small motion artifacts, for example, during glides or at the end of a lap. Based on this information, a heart rate model can be created.

Once both the work rate model 1720 and the heart rate model 1728 have been determined, and accordingly, a reliability of each of the models is determined, the appropriate model can be selected at model selection 1730. Model selection may depend upon errors in the stroke length, stroke rate, distance, and heart rate to determine which model is more accurate. Further, the models can be fused together to create a more accurate total of model of calorimetry.

Once the appropriate model for the swimming session has been determined, then the METs for that session also can be calculated.

Figure 18:
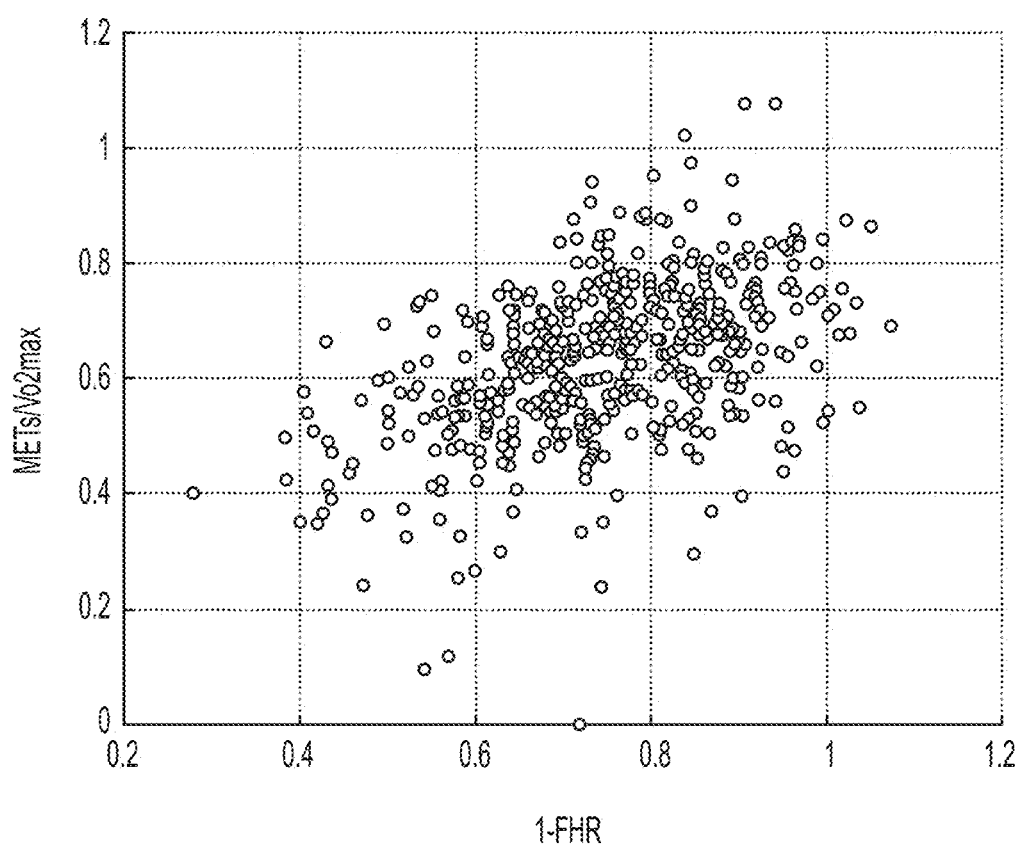
FIG. 18 is a plot of normalized METs vs. fractional heart rate, according to some embodiments of the present disclosure.

FIG. 18 is a plot of normalized METs vs. fractional heart rate, according to some embodiments of the present disclosure. The y axis shows METs/VO2max from 0.0 to 1.2 and the x axis is 1-Fractional Heart rate from 0.2 to 1.2. This plot shows a linear relationship between METs, normalized to VO2max, and fractional heart rate.

One difficulty in estimating energy expenditure of a user while swimming is how to distinguish glides and strokes. Glide detection can help to achieve more accurate calorimetry. For example, glides can cover up to 25% of a lap distance for some swimmers, in particular, efficient, experienced swimmers. Therefore, ignoring glides could lead to overestimates in energy expenditure, because glides may correspond to lower energy expenditure rate (i.e., lower MET) compared to strokes.

Glide detection can also help with the classifications of swimming styles. Based on information related to glide times, stroke rates, stroke patterns, and times for turns, the user's movement can be assigned to different styles (e.g., freestyle stroke, breaststroke, backstroke, butterfly stroke, etc.)

Glide detection can also help to provide more accurate lap times to the user. If the wearable device 100 or the companion device 300 can determine if the user is gliding, or stroking, or turning, the lap time can then be broken up into different parts, e.g., turn time, glide time, and stroke time. In this way, the user can review the data and assess his or her performances in further detail.

Figure 19:
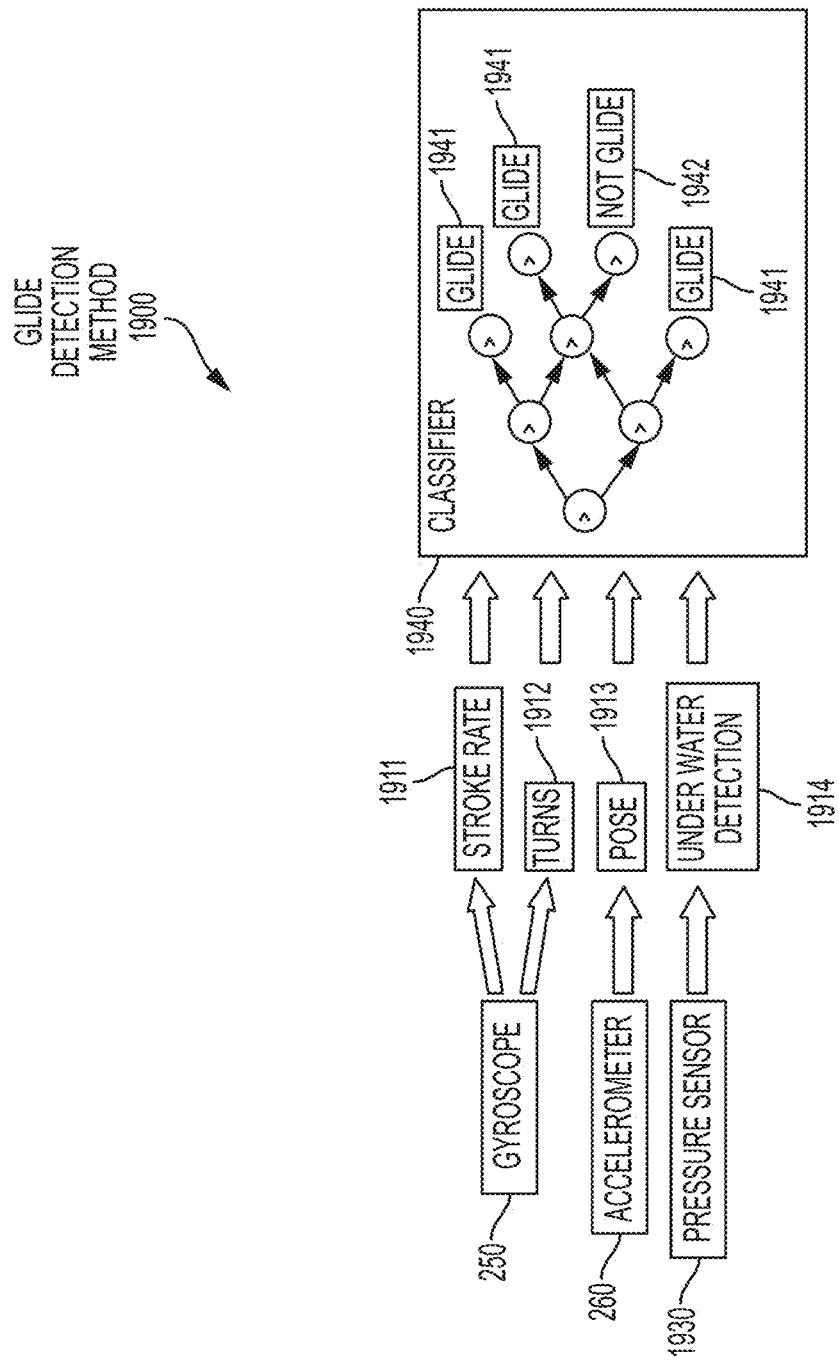
FIG. 19 illustrates a method of detecting glides of a user while the user is swimming according to some embodiments of the present disclosure.

FIG. 19 shows a method 1900 of detecting glides during swimming. In some embodiments, the detection method 1900 can use measurements data from a gyroscope 250 in the wearable device 100 (not shown). The gyroscope 250 may be a three-axis gyroscope that measures rotational data, such as rotational movement and/or angular velocity, in up to three-dimension (e.g., yaw, pitch, and roll). In some embodiments, the method 1900 can use measurements data from an accelerometer 260 in the wearable device 100. The accelerometer 260 may be a three-axis accelerometer that measures linear acceleration in up to three dimensions (e.g., x-axis, y-axis, and z-axis). In some embodiments, the method 1900 can use measurements data from a pressure sensor 1930 (e.g., an altimeter or barometer) in the wearable device 100. In some embodiments, wearable device 100 can include a classifier module 1940 (e.g., of the processor 210) which may determine whether the user is gliding based on the measurements data.

In some embodiments, the gyroscope 250 can measure rotational data and can provide information related to a user's stroke rate 1911. For example, during glides, a user usually does not stroke. Thus the angular velocity value measured by the gyroscope 250 may be smaller compared to angular velocity values measured during strokes. In some embodiments, the gyroscope 250 can provide information related to turns 1912. For example, a small or close to zero angular velocity value can indicate the user is not making a turn. The information related to stroke rate 1911 and turns 1912 may be sent to the classifier 1940.

In some embodiments, the accelerometer 260 can measure acceleration data and can provide information related to a pose 1913 of a user's wrist. For example, during gliding, the user usually keeps his or her wrists relatively still. Thus the direction of gravity remains relatively constant in the body-fixed frame of reference of the wearable device 100. The pose of the user's wrist can be determined based on the gravity direction. The information related to pose 1913 may be sent to the classifier 1940.

In some embodiments, the pressure sensor 1930 can measure pressure data and can provide information related to under water detection 1914. For example, during gliding, the user usually keeps his or her hands and/or arms under water. Thus, the pressure sensor 1930 may sense higher pressure due to the pressure from the water, which generally will be greater than pressure from the air. If the pressure sensor 1930 includes an altimeter, it may show a drop in elevation. The information related to under water detection 1914 may be sent to the classifier 1940. The under water detection 1914 can help to pick up spurious strokes while the user is not under water. For example, the user may walk around the pool or wipe hair, and the wearable device 100 may obtain rotational and acceleration data. However, the measurements by the pressure sensor 1930 may indicate the user may not be under water. Therefore, these strokes may not be regarded as swimming strokes.

In some embodiments, other methods can be used to detect if the user is under water. For example, wearable device 100 can have a pressure sensitive screen which can detect a pressure imposed on it. Based on the detected pressure, wearable device 100 and/or companion device 300 can determine if the user is under water. In some embodiments, wearable device 100 and/or companion device 300 can estimate a underwater depth based on the detected pressure.

In some embodiments, the classifier 1940 can determine whether or not the user is gliding based on the measurements data from one sensor or multiple sensors. The classifier 1940 can be a computer program executed by the processor in the wearable device 100 and/or the companion device 300 (not shown). The classifier 1940 can implement algorithms to classify the user's movements during a swimming session into different categories, e.g., glide 1941, or not glide 1942.

Figure 20:
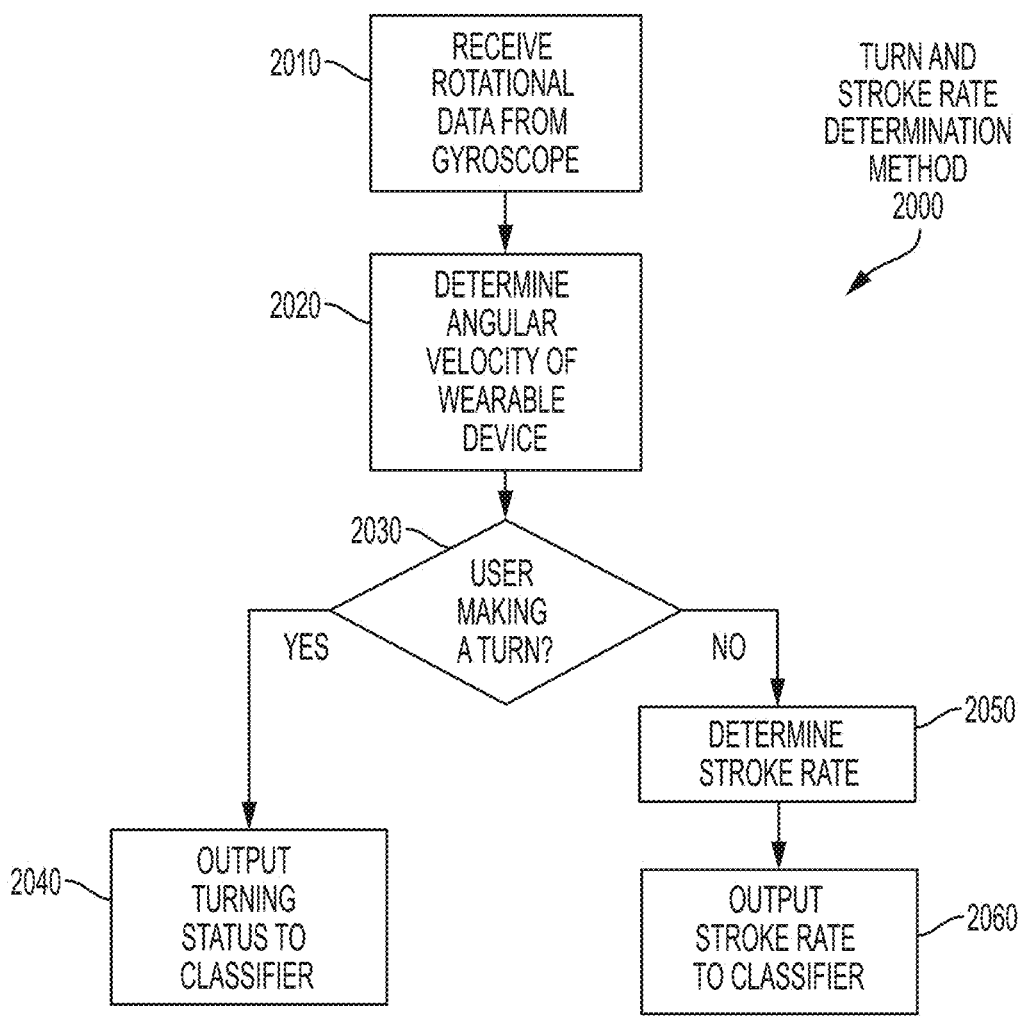
FIG. 20 illustrates a method of determining if a user is making a turn and the user's stroke rate according to some embodiments of the present disclosure.

FIG. 20 shows a method 2000 for determining whether a user is making a turn and the user's stroke rate according to some embodiments of the present disclosure. The user's turning status and stroke rate may be determined and used to detect if the user is gliding. In some embodiments, method 2000 can be modified by, for example, having steps combined, divided, rearranged, changed, added, and/or removed.

In the example described herein, method 2000 is performed by processor 210 of wearable device 100. However, in some embodiments, some or all steps may be performed by other elements (e.g., by a processor of a mobile device in communication with wearable device 100). The method 2000 may begin at step 2010.

At step 2010, three-dimensional rotational information may be received at the main processor 210 or motion co-processor 215 from the gyroscope 250 on a wearable device (e.g., wearable device 100) of a user. In some embodiments, rotational information may be filtered, such as by a low-pass filter, to remove unwanted noise from the ambient.

At step 2020, main processor 210 may determine angular velocity of wearable device 100 with respected to a frame of reference such as a body-fixed frame of reference or an inertial frame of reference.

At step 2030, main processor 210 may determine whether the user is making a turn from the angular velocity. If it is determined that the user is making a turn, the turn and stroke rate determination method 2000 may proceed to step 2040. At step 2040, the user's turning status may be outputted to the classifier of the processor 200 for further processing. The user's turning status may be one of the parameters the classifier uses to detect gliding.

If main processor 210 determines that the user is not making a turn, it may proceed to step 2050. At step 2050, the user's stroke rate can be determined based on the angular velocity collected from the gyroscope 250. Then at step 2060, the user's stroke rate may be outputted to the classifier for further processing. The user's stroke rate may be one of the parameters the classifier uses to detect gliding.

Figure 21:
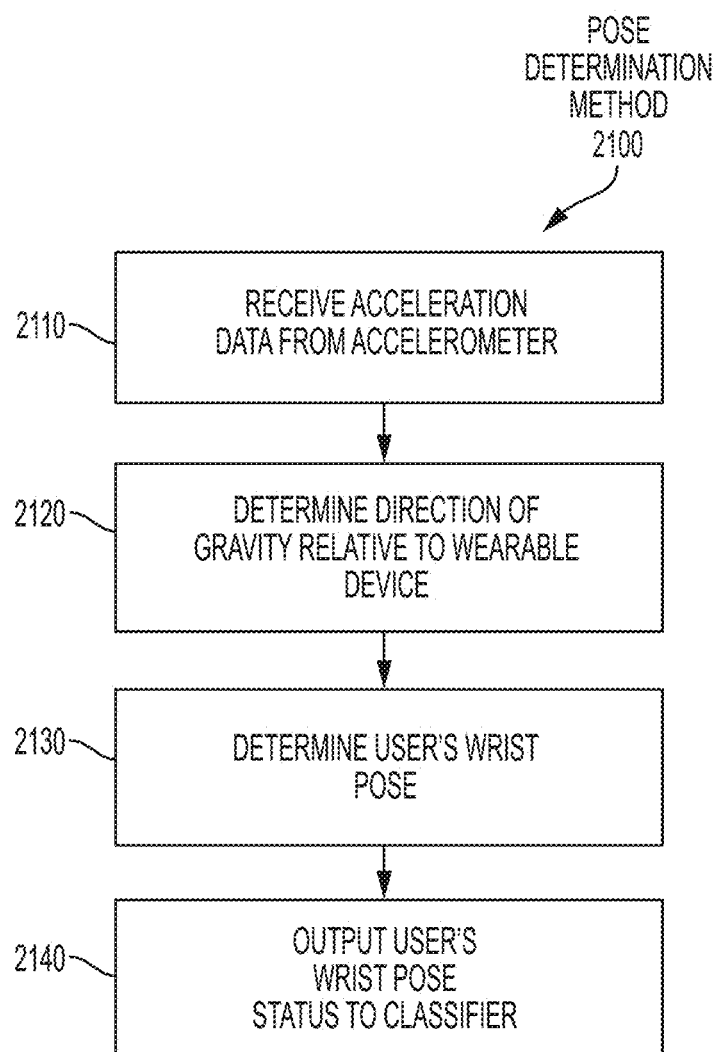
FIG. 21 illustrates a method of determining a pose of a user's wrist according to some embodiments of the present disclosure.

FIG. 21 shows a method 2100 for determining a pose of a user's wrist according to some embodiments of the present disclosure. The determined pose of the user's wrist may be used to detect gliding during swimming. In some embodiments, method 2100 can be modified by, for example, having steps combined, divided, rearranged, changed, added, and/or removed. In the example described herein, method 2100 is performed by main processor 210 of wearable device 100. However, in some embodiments, some or all steps may be performed by other elements (e.g., by a processor of a mobile device in communication with wearable device 100). Pose determination method 2100 may begin at step 2110.

At step 2110, three-dimensional acceleration information may be received at main processor 210 or motion co-processor 215 from the accelerometer 260 on a wearable device (e.g., wearable device 100) of a user. In some embodiments, acceleration information may be filtered, such as by a low-pass filter, to remove unwanted noise from the ambient.

At step 2120, main processor 210 or motion co-processor 215 may determine a direction of gravity relative to the wearable device 100 with respect to a frame of reference such as a body-fixed frame of reference or an inertial frame of reference.

At step 2130, main processor 210 may determine the pose of the user's wrist from the acceleration information and the gravity direction. For example, the user's wrist may be in a position such that display surface of the wearable device 100 may faces up toward the sky, parallel with the ground.

At step 2140, the pose information of the user's wrist may be outputted to the classifier of main processor 210 for further processing. The pose information may be one of the parameters the classifier uses to detect gliding.

Figure 22:
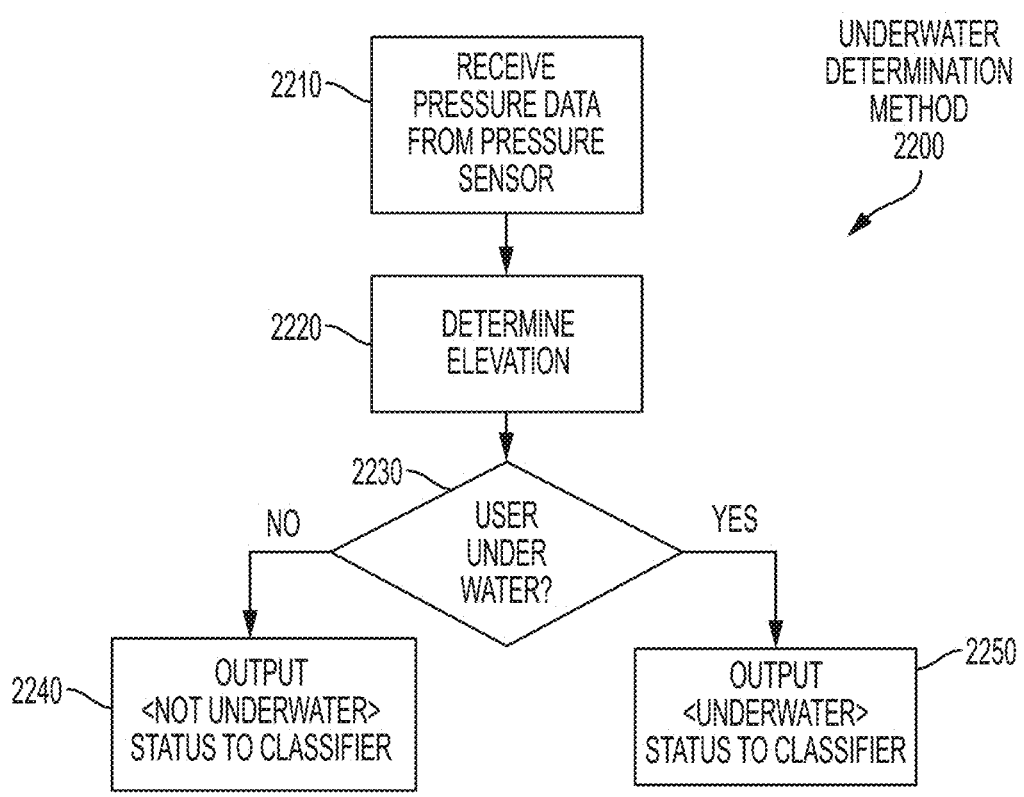
FIG. 22 illustrates a method of determining if a user is under water according to some embodiments of the present disclosure.

FIG. 22 shows a method 2200 for determining if a user is under water according to some embodiments of the present disclosure. The determined under water status may be used to detect gliding during swimming. In some embodiments, method 2200 can be modified by, for example, having steps combined, divided, rearranged, changed, added, and/or removed. In the example described herein, method 2200 is performed by processor 210 of wearable device 100. However, in some embodiments, some or all steps may be performed by other elements (e.g., by a processor of a mobile device in communication with wearable device 100). Underwater determination method 2200 may begin at step 2210.

At step 2210, pressure information may be received at main processor 210 or motion co-processor 215 from a pressure sensor on a wearable device (e.g., wearable device 100) of a user. In some embodiments, pressure information may be filtered, such as by a low-pass filter, to remove unwanted noise.

At step 2220, main processor 210 may determine an elevation of the wearable device 100 based on the received pressure data.

At step 2230, main processor 210 may determine if the user is under water. For example, if the elevation of the wearable device 100 has a sudden decrease, possibly due to additional pressure from water, main processor 210 may determine the user is under water. If it is determined that the user is not under water, the status may be outputted to the classifier for further processing at step 2240. If it is determined that the user is under water, the status may be outputted to the classifier for further processing at step 2250. The status may be one of the parameters the classifier uses to detect gliding.

Figure 23A:
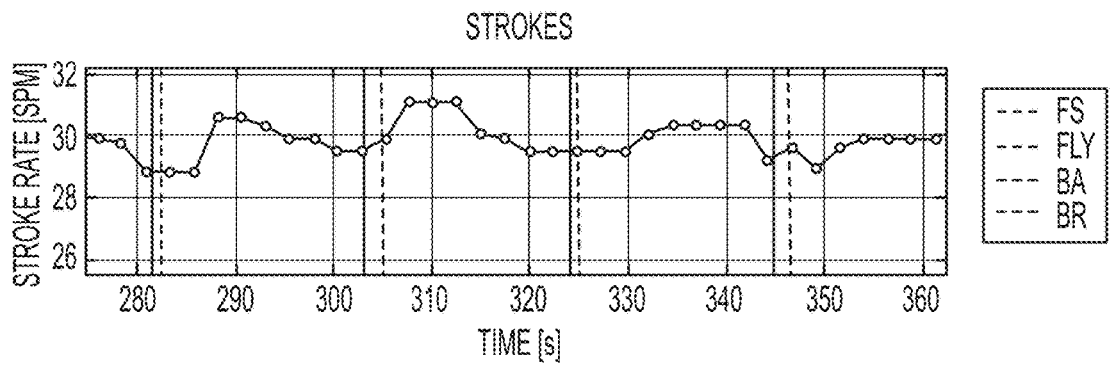
FIGS. 23A-23C show plots of stroke rate, pressure, and pose information of an example user's swimming session according to some embodiments of the present disclosure.
Figure 23B:
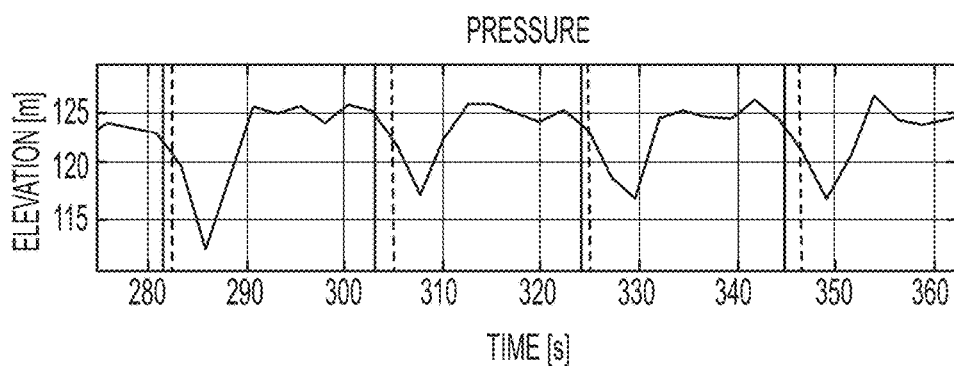
Figure 23C:
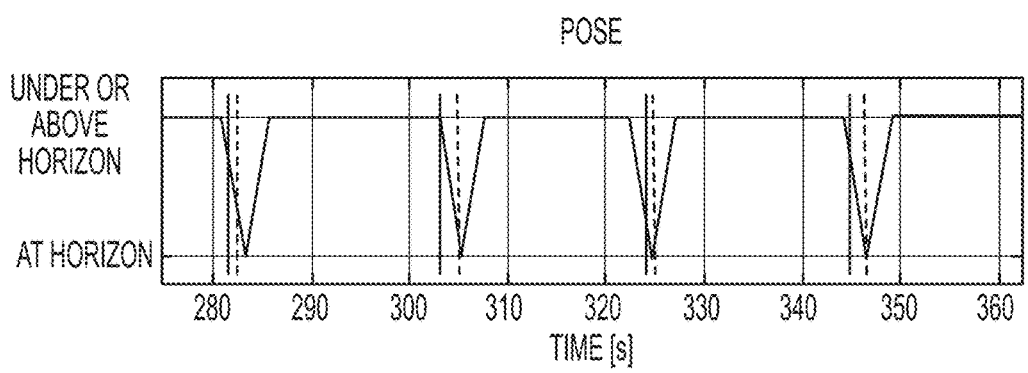

FIGS. 23A-23C show examples of measured data during a user's swimming session in a pool. The horizontal time axes in the three figures are synchronized. The dashed vertical lines mark the time when the user started from one end of the pool and the solid vertical lines mark the time when the user reached the other end of the pool. FIG. 23A shows the stroke rates as a function of time. The decrease in the stroke rate may be attributed to glides because most of the user's motions may be full body undulations during glides. FIG. 23B shows the measured elevation from the pressure sensor as a function of time. The elevation dips may correspond to glides because the user is under water during glides and the pressure increase leads to an observable decrease of elevation. As the user's hands exit the water, the pressure decreases and the elevation increases. FIG. 23C shows the pose information as a function of time. The pose of the user's wrist during the glide undulations is mostly in line with the horizon and under or above horizon during the strokes.

It is to be understood that the present disclosure is not limited in its application to the details of construction and to the arrangements of the components set forth in the description or illustrated in the drawings. The present disclosure is capable of other embodiments and of being practiced and carried out in various ways. In addition, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, systems, methods and media for carrying out the several purposes of the present disclosure. It is important, therefore, that the claims be regarded as including such equivalent constructions insofar as they do not depart from the spirit and scope of the present disclosure.

Although the present disclosure has been described and illustrated in the foregoing exemplary embodiments, it is understood that the present disclosure has been made only by way of example, and that numerous changes in the details of implementation of the present disclosure may be made without departing from the spirit and scope of the present disclosure, which is limited only by the claims which follow.

What is claimed is:

1. A method for improving an accuracy of a wearable device while estimating energy expenditure of a user during a swimming session, the method comprising:
   collecting, by a motion sensing module of a wearable device, motion data of the user;
   determining, by a processor circuit of the wearable device, rotational data of the user based on the motion data;
   counting, by the processor circuit, a number of strokes made by the user based on the set of rotational data;
   estimating, by the processor circuit, a stroke rate of the user based on the number of strokes;
   counting, by the processor circuit, a number of laps finished by the user based on the set of rotational data;
   calculating, by the processor circuit, a stroke length based on the number of strokes, the number of laps finished, and a lap length associated with the swimming session;
   calculating, by the processor circuit, a speed of the user based on the stroke rate and the stroke length;
   estimating, by the processor circuit, an efficiency of the user based on at least one of the stroke length or a level of stroke orbit consistency of the user;
   classifying, by the processor circuit, a swimming style of the user based on the set of rotational data;
   determining, by the processor circuit, an energy expenditure of the user based on the speed, efficiency, and swimming style of the user; and
   outputting, by the processor circuit, the determined energy expenditure of the user.

2. The method of claim 1, wherein the motion data is expressed in a first frame of reference and the rotation data is expressed in a second frame of reference.

3. The method of claim 1, comprising:
   receiving, by the processor circuit, one or more inputs from the user, wherein the one or more inputs from the user comprise at least one of the user's gender, age, height, weight, or body mass index;
   adjusting, by the processor circuit, the energy expenditure of the user based on the received one or more inputs; and
   outputting, by the processor circuit, the adjusted energy expenditure of the user.

4. The method of claim 1, comprising:
   measuring, by a heart rate sensing module of the user wearable device, a heart rate of the user;
   determining, by the processor circuit, a fraction of heart rate reserve (FHR) of the user based on the measured heart rate;
   estimating, by the processor circuit, the user's anaerobic energy expenditure based on at least one of the FHR, the stroke length, the stroke rate, or the speed; and
   determining, by the processor circuit, the energy expenditure of the user based on the estimated anaerobic energy expenditure.

5. The method of claim 1, comprising:
   measuring, by a heart rate sensing module of the wearable device, a heart rate of the user;

determining, by the processor circuit, a fraction of heart rate reserve (FHR) of the user based on the measured heart rate;

determining, by the processor circuit, a maximal oxygen uptake of the user; and determining, by the processor circuit, a heart rate model based on FHR and the maximal oxygen uptake, wherein determining the energy expenditure of the user based on the heart rate model.

6. The method of claim 1, wherein calculating the speed of the user comprises:

receiving, by a GPS sensor of the wearable device, location data of the user during the swimming session; and calculating, by the processor circuit, a stroke length and a speed of the user based on the received location data.

7. The method of claim 1, wherein the motion sensing module comprises at least one of a gyroscope or an accelerometer.

8. The method of claim 1, comprising:

detecting, by the processor circuit, one or more glides of the user during the swimming session; and determining, by the processor circuit, the energy expenditure of the user based on the detected one or more glides.

9. The method of claim 8, wherein detecting the one or more glides of the user comprises:

determining, by the processor circuit, whether the user is making a turn based on the set of rotational data;

detecting, by the processor circuit, a pose angle of the user's wrist based on the set of rotational data;

determining, by the processor circuit, whether the user is under water using pressure data received from a pressure sensor of the wearable device; and detecting, by the processor circuit, one or more glides of the user based on the stroke rate, the pose of the user's wrist, whether the user is making a turn, and whether the user is under water.

10. The method of claim 9, wherein detecting a pose angle of the user's wrist comprises:

determining, by the processor circuit, a direction of gravity relative to the user device based on the motion data;

detecting, by the processor circuit, a pose angle of the user's wrist based on the direction of gravity.

11. The method of claim 9, wherein determining whether the user is under water comprises:

determining, by the processor circuit, an elevation of the wearable device based on the pressure data; and determining, by the processor circuit, whether the user is under water based on the determined elevation.

12. A system for improving an accuracy of a wearable device while estimating energy expenditure of a user during a swimming session, the system comprising:

a motion sensing module configured to collect motion data of the user;

a processor circuit in communication with the motion sensing module and configured to execute instructions causing the processor circuit to:

determine rotational data of the user base on the motion data;

count a number of strokes made by the user based on the set of rotational data;

estimate a stroke rate of the user based on the number of strokes;

count a number of laps finished by the user based on the set of rotational data;

estimate a stroke length based on the number of strokes, the number of laps finished, and a lap length associated with the swimming session;

estimate a speed of the user based on the stroke rate and the stroke length;

estimate efficiency of the user based on at least one of the stroke length or a level of stroke orbit consistency of the user;

classify a swimming style of the user based on the set of rotational data;

determine an energy expenditure of the user based on the speed, efficiency, and swimming style of the user; and output the determined energy expenditure of the user.

13. The system of claim 12, wherein the instructions further cause the processor circuit to:

receive one or more inputs from the user, wherein the one or more inputs from the user comprise at least one of the user's gender, age, height, weight, or body mass index;

adjust the determined energy expenditure of the user based on the received one or more inputs; and output the adjusted energy expenditure of the user.

14. The system of claim 12, further comprising a heart rate sensing module configured to measure a heart rate of the user.

15. The system of claim 14, wherein the instructions further cause the processor circuit to:

determine, a fraction of heart rate reserve (FHR) of the user based on the measured heart rate; determine, a maximal oxygen uptake of the user;

determine, a heart rate model based on the FHR and the maximal oxygen uptake; and determine, the energy expenditure of the user based on the heart rate model.

16. The system of claim 12, further comprising a GPS sensor configured to receive location data of the user.

17. The system of claim 16, wherein the instructions further cause the processor circuit to:

estimate a stroke length and a speed of the user based on the received location data of the user.

18. The system of claim 12, wherein the motion sensing module comprises at least one of a gyroscope or an accelerometer.

19. The system of claim 12, wherein the instructions further cause the processor circuit to:

determine whether the user is making a turn based on the set of rotational data;

detect a pose of the user's wrist based on the set of rotational data;

determine whether the user is under water based on pressure data received from a pressure sensor of the wearable device;

determine whether the user is gliding while swimming based on the stroke rate, the pose of the user's wrist, whether the user is making a turn, and whether the user is under water;

adjust the energy expenditure of the user based on the determined glide; and output the adjusted energy expenditure of the user.

* * * * *